United States Patent
Hesse et al.

[11] Patent Number: 5,811,562
[45] Date of Patent: Sep. 22, 1998

[54] VITAMIN-D AMIDE DERIVATIVES

[75] Inventors: Robert Henry Hesse, Winchester; Sundara Katugam Srinivasasetty Setty, Cambridge, both of Mass.

[73] Assignee: Research Institute for Medicine and Chemistry Inc., Cambridge, Mass.

[21] Appl. No.: 704,613

[22] PCT Filed: Mar. 23, 1995

[86] PCT No.: PCT/GB95/00658

§ 371 Date: Nov. 20, 1996

§ 102(e) Date: Nov. 20, 1996

[87] PCT Pub. No.: WO95/25718

PCT Pub. Date: Sep. 28, 1995

[30] Foreign Application Priority Data

Mar. 23, 1994 [GB] United Kingdom .................. 9405715

[51] Int. Cl.⁶ ........................ C07C 401/00; A01N 45/00
[52] U.S. Cl. ............................. 552/653; 514/167
[58] Field of Search ........................ 552/653; 546/226; 514/167

[56] References Cited

FOREIGN PATENT DOCUMENTS

| 42 34 382 | 4/1994 | Germany | C07C 401/00 |
| 93/09093 | 5/1993 | WIPO | C07C 401/00 |
| 93/19044 | 9/1993 | WIPO | C07C 401/00 |
| 94/26707 | 11/1994 | WIPO | C07C 401/00 |

Primary Examiner—S. Mark Clardy
Assistant Examiner—Alton Pryor
Attorney, Agent, or Firm—Bacon & Thomas

[57] ABSTRACT

The present invention relates to compounds of general formula (I)

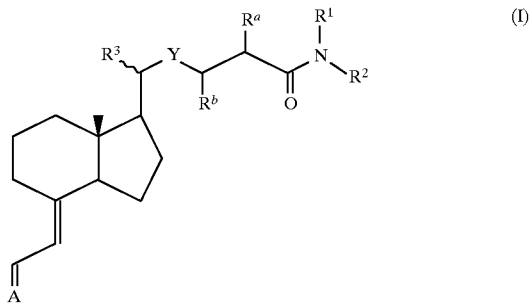

where $R^1$ and $R^2$, which may be the same or different, each represent a hydrogen atom or an aliphatic, cycloaliphatic, araliphatic or aryl group or together with the nitrogen atom to which they are attached form a heterocyclic group; $R^3$ represents a methyl group having α- or β-configuration; one of $R^a$ and $R^b$ represents a hydroxy group or protected hydroxy group and the other represents a hydrogen atom; Y represents a valence bond or an alkylene group containing up to 3 carbon atoms; and A= represents a cyclohexylidene moiety characteristic of the A-ring of a 1α-hydroxylated vitamin D or analogue thereof. Active compounds of the invention exhibit separation of cell modulating and calcaemic activities coupled with enhanced duration of activity.

13 Claims, No Drawings

VITAMIN-D AMIDE DERIVATIVES

This invention relates to novel vitamin D analogues, more particularly to 1α-hydroxy vitamin $D_3$ analogues having a modified side chain at the 17-position.

Vitamin $D_3$ which has the formula

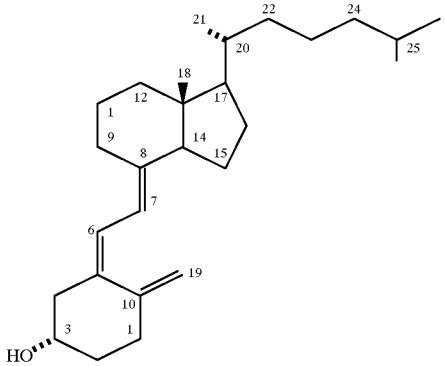

is well known to play a vital role in the metabolism of calcium, by promoting intestinal absorption of calcium and phosphorus, maintaining adequate serum levels of calcium and phosphorus and stimulating mobilisation of calcium from the bone fluid compartment in the presence of parathyroid hormone.

Following the discovery that the D vitamins are hydroxylated in vivo, at the 25-position in the liver and at the 1α-position in the kidney, the resulting 1 α,25-dihydroxy metabolite being the biologically active material, much attention has been given to hydroxylated vitamin D analogues, initially with the intention of achieving enhanced effects on calcium metabolism. The subsequent findings that 1α,25-dihydroxy vitamin $D_3$ exhibits cell modulating activity, including immunosuppressive and immunopotentiating effects, led to further investigations in a search for analogues exhibiting a high level of such activity coupled with a reduced effect on calcium metabolism, since the use of such compounds for cell modulating purposes may otherwise be precluded by unacceptable hypercalcaemia and cumulative toxicity problems as a result of their effects on calcium metabolism.

A review of previous work in this area is contained in WO 93/09093, the contents of which are incorporated herein by reference. This review identifies a number of vitamin D analogues which appear to show cell modulating activity at a similar level to that of 1α,25-dihydroxy vitamin $D_3$; however, these analogues also appear still to show appreciable effects on calcium metabolism, such activity being attenuated by at most two orders of magnitude relative to that of 1α,25-dihydroxy vitamin $D_3$. Use of such analogues may therefore give rise to cumulative toxicity problems if the compounds are used in long term therapy, particularly where systemic application is required.

It has been suggested that the attenuated calcium effect of such vitamin D analogues may in fact be due merely to more rapid metabolism of the analogue, this reducing the amount of the drug circulating in the body (see e.g. Bouillon et al., J. Bone Miner. Res. (1991), 6, p 1051 and Dusso et al., Endocrinology (1991), 128, p 1687). The cell modulating effect may similarly be reduced in vivo so that one may require larger systemic dosages than are suggested by in vitro test results.

In the above-mentioned WO 93/09093 there are described and claimed a number of 1α-hydroxy vitamin D derivatives and 20-epi analogues thereof in which the 17-position side chain terminates in an optionally N-substituted or N,N-disubstituted carbamoyl group. Such vitamin D amide derivatives exhibit minimal effect on calcium metabolism, e.g. having insignificant effects on serum calcium and phosphorus levels in rats even when administered in amounts of 100 times a conventional dosage for 1α,25-dihydroxy vitamin $D_3$, but may have a potent cell modulating effect, for example as evidenced by eliciting cell differentiation and maturation, inhibiting proliferation and/or by activating monocytes; they accordingly exhibit an advantageous therapeutic ratio of cell modulating to calcaemic activity. The cell modulating activity of the compounds is most surprising given that they possess sizeable vitamin D-like side chains which do not carry a hydroxyl group at the 24- or 25-positions and which in many cases are not capable of being hydroxylated at these positions; previous findings had strongly suggested the need for such a hydroxyl group in order to obtain cell modulating activity. Furthermore, other workers had found the presence of an amide group in the 17-position side chain of corresponding 1α-unsubstituted compounds to have an antagonist effect characterised by anti-vitamin D activity (see U.S. Pat. No. 4,217,288).

The present invention is based on the finding that 1α-hydroxy vitamin D derivatives in which the 17-position side chain is a saturated group which terminates in an amide grouping and which carries a hydroxyl group α- or β-relative to the amide function may exhibit a particularly useful combination of biological properties, e.g. as represented by a good separation of cell modulating and calcaemic activities coupled with an enhanced duration of activity. This latter property is especially surprising since such compounds might be thought to correspond to metabolic degradation products which would be expected to be more rapidly eliminated from the system than corresponding non-side chain hydroxylated vitamin D amide derivatives.

Thus according to one aspect of the present invention there are provided compounds of general formula (I)

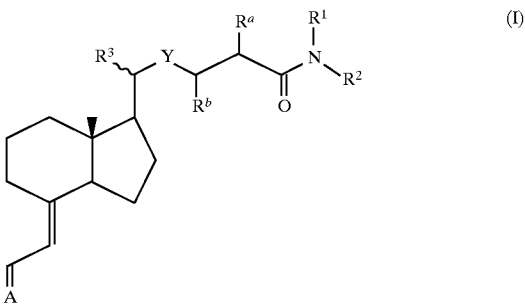

(where $R^1$ and $R^2$, which may be the same or different, each represent a hydrogen atom or an aliphatic, cycloaliphatic, araliphatic or aryl group or together with the nitrogen atom to which they are attached form a heterocyclic group; $R^3$ represents a methyl group having α- or β-configuration; one of $R^a$ and $R^b$ represents a hydroxy group or protected hydroxy group and the other represents a hydrogen atom; Y represents a valence bond or an alkylene group containing up to 3 carbon atoms; and A= represents a cyclohexylidene moiety characteristic of the A-ring of a 1α-hydroxylated vitamin D or analogue thereof).

Aliphatic groups represented by $R^1$ and $R^2$ may, for example, include lower alkyl groups, for example containing up to 6 carbon atoms, e.g. as in methyl, ethyl, propyl and butyl groups. Cycloaliphatic groups may, for example, include lower cycloalkyl, for example containing 3–8 carbon atoms, e.g. as in cyclopropyl, cyclopentyl and cyclohexyl groups. Araliphatic groups may, for example, include $C_{6-12}$ aryl $C_{1-4}$ alkyl groups such as benzyl or phenethyl. Aryl groups may, for example, include $C_{6-12}$ carbocyclic aryl groups such as phenyl or naphthyl, optionally carrying one or more substituents, for example selected from halo (e.g. chloro or bromo), lower (e.g. $C_{1-4}$) alkyl such as methyl, lower alkoxy (e.g. methoxy), lower alkanoyl (e.g. acetyl), lower alkylamino (e.g. methylamino), di(lower alkyl) amino (e.g. dimethylamino), nitro, carbamoyl, and lower alkanoylamino (e.g. acetamido).

Where the group $R^1R^2N-$ represents a heterocyclic group this may, for example, contain one or more further heteroatoms selected from O, N and S and may comprise one or more rings, e.g. each having 5 or 6 ring members, for example as in N-attached pyrrolyl, pyrazolyl, imidazolyl, indolyl, indazolyl, purinyl, pyrrolidinyl, imidazolidinyl, pyrazolidinyl, piperidinyl, morpholino, thiazolidinyl and thiamorpholino groups.

Where $R^3$ in formula (I) is a methyl group in the α-configuration the compounds have the 20R configuration characteristic of natural vitamin D derivatives; where $R^3$ is in the β-configuration the compounds have the 20S configuration of epi-vitamin D derivatives. It will be appreciated that the invention also embraces mixtures of the two isomers, as well as individual isomers and mixtures of isomers resulting from the presence of an optical centre in the side chain at the point of attachment of the hydroxyl group $R^a$ or $R^b$.

The cyclohexylidene ring represented by A= will normally carry hydroxyl groups or protected derivatives thereof at the 1α- and 3α-positions, and may carry further substituents, e.g. which tend to enhance antiproliferative activity and/or stimulate differentiation. A= may thus, for example, be represented by the formula (A-1)

where $R^4$ and $R^5$, which may be the same or different, each represent a hydrogen atom or an O-protecting group, and $R^6$ and $R^7$, which may the same or different, are selected from hydrogen atoms and appropriate mono- or di-valent substituting groups.

Where any of $R^a$, $R^b$, $R^4$ and $R^5$ represent O-protecting groups these may, for example, be cleavable O-protecting groups such as are commonly known in the art. Suitable groups include etherifying groups such as silyl groups (e.g. tri (lower alkyl) silyl groups such as trimethylsilyl, triethylsilyl, triisopropylsilyl or t-butyldimethylsilyl; tri (aryl) silyl groups such as triphenylsilyl; and mixed alkylarylsilyl groups); lower (e.g. $C_{1-6}$) alkyl groups optionally interrupted by an oxygen atom, such as methyl, methoxymethyl or methoxyethoxymethyl; and cyclic groups such as tetrahydropyranyl. Esterifying O-protecting groups include lower (e.g. $C_{1-6}$) alkanoyl such as acetyl, propionyl, isobutyryl or pivaloyl; aroyl (e.g. containing 7–15 carbon atoms) such as benzoyl or 4-phenylazobenzoyl; lower alkane sulphonyl such as (optionally halogenated) methane sulphonyl; and arene sulphonyl such as p-toluene sulphonyl.

O-protected derivatives are useful as intermediates in the preparation of active compounds of general formula (I) where $R^4$ and $R^5$ represent hydrogen atoms and one of $R^a$ and $R^b$ represents a hydroxyl group. Esterification or other protection of the side chain hydroxyl group $R^a$ or $R^b$ may also be of assistance when it is desired to separate stereoisomers of compounds (I) where, as will usually be the case, introduction of the side chain hydroxyl group creates an optical centre. It will be appreciated that, in general, where any O-protecting groups are metabolically labile in vivo, such ethers and esters of formula (I) may be useful directly in therapy, as may be ethers in which $R^a$ or $R^b$ represent lower alkoxy groups.

At least one of $R^6$ and $R^7$ in formula (A-1) above is advantageously a hydrogen atom. Substituents which may be present as the other of $R^6$ and $R^7$ include, for example, methylene, methyl and ethylene (so as to form a spiro-linked cyclopropyl group with the attached carbon atom).

Representative A= groups falling within the above formula (A-1) include the following:

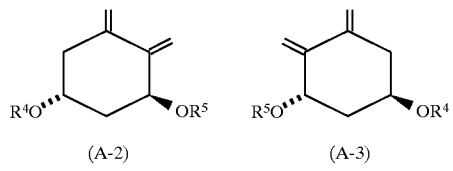

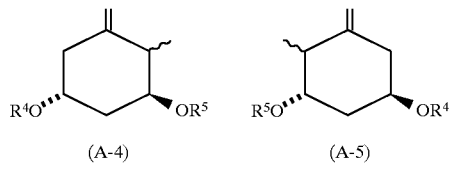

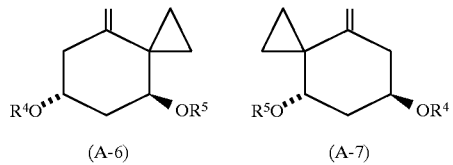

and

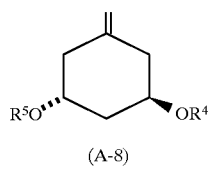

It will be appreciated that compounds containing groups (A-2) and (A-3) are respectively 5,6-cis (i.e. 5Z) and 5,6-trans (i.e. 5E) isomers of vitamin D analogues. Compounds containing groups (A-4) and (A-5) are similarly 5,6-cis and 5,6-trans isomers respectively of 10,19-dihydro vitamin D analogues, and compounds containing group (A-8) are 19-nor vitamin D analogues.

5,6-Trans isomers according to the invention are principally of interest as intermediates in the preparation of corresponding 5,6-cis isomers, e.g. as described in greater detail hereinafter. However, 5,6-trans isomers in which $R^4$ and $R^5$ are hydrogen atoms or metabolically labile groups will often exhibit biological activity, e.g. at about one order of magnitude less than corresponding 5,6-cis isomers, and may thus be useful in therapy.

Active compounds of formula (I) exhibit cell modulating activity, e.g. as evidenced by eliciting cell differentiation and maturation, inhibiting proliferation and/or by activating monocytes (e.g. as estimated by the method of Styrt et al., Blood (1986), 67, pp 334–342), while possessing suppressed calcaemic activity relative to compounds such as 1α-hydroxy vitamin $D_3$, e.g. as evidenced by low effects on serum calcium and phosphorus levels in rats; they may accordingly exhibit an advantageous therapeutic ratio of cell modulating to calcaemic activity. As noted above they may also exhibit enhanced duration of activity compared to prior art compounds.

The cell modulating activity of such active compounds according to the invention, combined with a substantial lack of calcaemic effect, render them of interest (both alone and as adjuncts) in the management of neoplastic disease, particularly myelogenous leukemias and pulmonary neoplasia, and suggest their use as agents to promote wound healing. They may also be used either alone or as adjuncts in the chemotherapy of infection and in all other therapeutic modalities in which mononuclear phagocytes are involved, for example in treatment of bone disease (e.g. osteoporosis, osteopenia and osteodystrophy as in rickets or renal osteodystrophy), autoimmune diseases, host-graft reaction, transplant rejection, inflammatory diseases (including modulation of immunoinflammatory reactions), neoplasias and hyperplasias, myopathy, enteropathy and spondylitic heart disease. Such active compounds according to the invention may also be useful in suppression of parathyroid hormone (e.g. as in serum calcium homeostasis), in treatment of dermatological diseases (for example including acne, alopecia, eczema, pruritus, psoriasis and skin aging, including photoaging), hypertension, rheumatoid arthritis, psoriatic arthritis, secondary hyperparathyrodism, asthma, cognitive impairment and senile dementia (including Alzheimer's disease), in fertility control in both human and animal subjects, and in management of disorders involving blood clotting, e.g. by dissolution of existing clots and/or prevention of clotting. The invention embraces use of these compounds in the therapy or prophylaxis of such conditions and in the manufacture of medicaments for such treatment or prophylaxis.

We believe that the active 20R isomers of such compounds of formula (I) may be preferred for treatment of infections, e.g. in combination therapy, whereas the active 20S epi-isomers may be preferred for applications involving an immunosuppressive effect, e.g. in treatment of autoimmune and inflammatory diseases, rheumatoid arthritis, diabetes, asthma etc. This view is supported by, for example, the work of Binderup et al. concerning 20-epi-vitamin $D_3$ analogues reported in *Biochemical Pharmacology* (1991), 42(8), pp 1569–1575.

Such effects on calcium metabolism and bone calcium mobilisation as are shown by active compounds of the invention may usefully be employed in applications such as, for example, treatment of bone disease.

It has been reported (Neef et al., 9th Workshop on Vitamin D (1994)) that in the case of vitamin D compounds having conventional terminally hydroxylated 17-position side chains (including side chains containing a heteroatom at the 23-position), analogues having 20,20-dimethyl, 20-methylene or 20-spirocyclopropyl groups may exhibit useful biological activity, typically resembling that of the corresponding 20R methyl-substituted isomer rather than the corresponding 20S epi-isomer. The present invention embraces analogues of the above-defined compounds of formula (I) wherein $R^3$ is selected from dimethyl, methylene or spirocyclopropyl groups.

Active compounds according to the invention may be formulated for administration by any convenient route, e.g. orally (including sublingually), parenterally, rectally or by inhalation; pharmaceutical compositions so formulated comprise a feature of the invention.

Orally administrable compositions may, if desired, contain one or more physiologically compatible carriers and/or excipients and may be solid or liquid. The compositions may take any convenient form including, for example, tablets, coated tablets, capsules, lozenges, aqueous or oily suspensions, solutions, emulsions, syrups, elixirs and dry products suitable for reconstitution with water or another suitable liquid vehicle before use. The compositions may advantageously be prepared in dosage unit form. Tablets and capsules according to the invention may, if desired, contain conventional ingredients such as binding agents, for example syrup, acacia, gelatin, sorbitol, tragacanth or polyvinyl-pyrollidone; fillers, for example lactose, sugar, maize-starch, calcium phosphate, sorbitol or glycine; lubricants, for example magnesium stearate, talc, polyethylene glycol or silica; disintegrants, for example potato starch; or acceptable wetting agents such as sodium lauryl sulphate. Tablets may be coated according to methods well known in the art.

Liquid compositions may contain conventional additives such as suspending agents, for example sorbitol syrup, methyl cellulose, glucose/sugar syrup, gelatin, hydroxymethylcellulose, carboxymethylcellulose, aluminium stearate gel or hydrogenated edible fats; emulsifying agents, for example lecithin, sorbitan monooleate or acacia; non-aqueous vehicles, which may include edible oils, for example vegetable oils such as arachis oil, almond oil, fractionated coconut oil, fish-liver oils, oily esters such as polysorbate 80, propylene glycol, or ethyl alcohol; and preservatives, for example methyl or propyl p-hydroxybenzoates or sorbic acid. Liquid compositions may conveniently be encapsulated in, for example, gelatin to give a product in dosage unit form.

Compositions for parenteral administration may be formulated using an injectable liquid carrier such as sterile pyrogen-free water, sterile peroxide-free ethyl oleate, dehydrated alcohol or propylene glycol or a dehydrated alcohol/propylene glycol mixture, and may be injected intravenously, intraperitoneally or intramuscularly.

Compositions for rectal administration may be formulated using a conventional suppository base such as cocoa butter or another glyceride.

Compositions for administration by inhalation are conveniently formulated for self-propelled delivery, e.g. in metered dose form, for example as a suspension in a propellant such as a halogenated hydrocarbon filled into an aerosol container provided with a metering dispense valve.

It may be advantageous to incorporate an antioxidant, for example ascorbic acid, butylated hydroxyanisole or hydroquinone in the compositions of the invention to enhance their storage life.

Where any of the above compositions are prepared in dosage unit form these may for example contain 0.1–500 μg, e.g. 0.2–100 μg, of active compound according to the invention per unit dosage form. The compositions may if desired incorporate one or more further active ingredients.

A suitable daily dose of an active compound according to the invention may for example be in the range 0.2–1000 μg, e.g. 0.4–200 μg, per day, depending on factors such as the severity of the condition being treated and the age, weight and condition of the subject.

Compounds according to the invention may be prepared by any convenient method, for example one of the following:

A) 5,6-Cis compounds of formula (I) may be prepared by isomerisation of a corresponding 5,6-trans compound, followed if necessary and/or desired by removal of any O-protecting groups. Isomerisation may be effected by, for example, treatment with iodine, with a disulphide or diselenide, or by irradiation with ultraviolet light, preferably in the presence of a triplet sensitiser.

B) 5,6-Trans compounds of formula (I) may be prepared by hydroxylating a corresponding 1-unsubstituted-5,6-trans compound, e.g. a compound (I) having an A= group of the formula

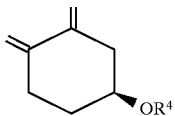
(A-9)

(where $R^4$ is hydrogen or an O-protecting group). Such hydroxylation may be effected using a selenite ester (which may be generated in situ by reaction of selenium dioxide or selenous acid and an alcohol), e.g. as described in GB-A-2038834, or using selenous acid at a pH in the range 3–9, e.g. as described in GB-A-2108506; the contents of both these specifications are incorporated herein by reference. The 1-unsubstituted-5,6-trans compound may, if desired, be prepared by isomerisation of the corresponding 5,6-cis vitamin in situ under the conditions of the oxidation.

C) By reaction of a compound containing a precursor for the desired 17-position side chain in one or more stages and with one or more reactants serving to form the desired side chain, followed if necessary and/or desired by isomerisation and/or removal of O-protecting groups.

Thus, for example, compunds of formula (I) in which $R^b$ represents a hydroxyl group may be prepared by reacting a compound of general formula (II)

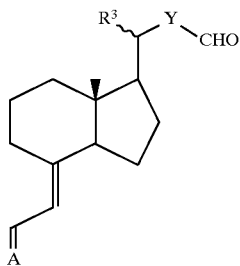
(II)

(where $R^3$, Y and A= are as hereinbefore defined, A= preferably being one of the groups (A-2)–(A-8) in O-protected form) with a metalated or dimetalated salt of an amide of general formula (III)

$CH_3 \cdot CO \cdot NR^1R^2$ (III)

(where $R^1$ and $R^2$ are as hereinbefore defined), e.g. an alkali metal salt such as a lithium salt prepared by reaction of the amide (III) with a base such as lithium diisopropylamide.

Alternatively one may prepare a precursor of a desired β-hydroxyamide derivative of general formula (I), e.g. a corresponding acid, ester, thioester or nitrile, and convert this to the desired compound (I), e.g. by direct aminolysis of an ester or thioester or via the corresponding free acid (e.g. obtained by hydrolysis of an ester, thioester or nitrile) or an acid halide obtained therefrom; it will be appreciated that nitrites may be partially hydrolysed to compounds (I) in which $R^1$ and $R^2$ are both hydrogen atoms. Reagents which may be used in the preparation of such precursors include appropriate metalated esters, dimetalated acids, silyl ketene acetals, oxazolones, oxazoles and Reformatski reagents such as α-bromoesters.

Compounds of general formula (I) in which $R^a$ represents a hydroxyl group may, for example, be prepared by direct hydroxylation of a compound of general formula (IV)

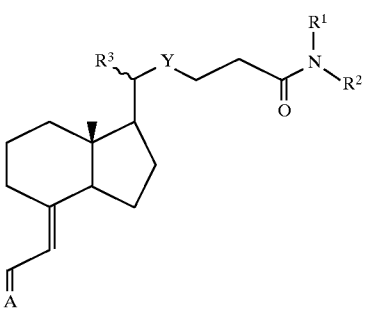
(IV)

(where $R^1$, $R^2$, $R^3$, Y and A= are as hereinbefore defined), e.g. by autoxidation of a metalated (e.g. lithiated) derivative by air or oxygen in the presence of a trivalent phosphorus compound such as triphenylphosphine or by peracid oxidation of a silylated derivative.

Alternatively one may employ a precursor for an amide of general formula (IV) such as a corresponding ester and convert the resulting α-hydroxyester to a corresponding amide, e.g. as described above.

Compounds (I) in which $R^a$ represents a hydroxyl group may also be prepared by reaction of a compound of general formula (V)

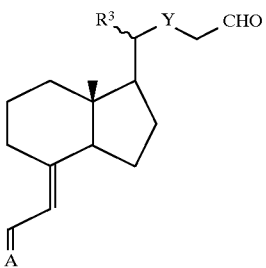
(V)

(where $R^3$, Y and A= are as hereinbefore defined) with an acyl anion (i.e. an anionic precursor for an acyl group, for example cyanide ion) and converting the product so obtained to the desired amide, e.g. via a corresponding acid or ester, for example as described above.

α-Hydroxyamides of general formula (I) may also be prepared by reduction of corresponding α-ketoamides or precursors therefor, e.g. α-ketoesters. Such techniques may be of advantage in permitting stereoselective synthesis of a desired stereoisomer, for example using reagents such as chiral boranes to effect stereoselective reduction of an α-ketoester and converting the product to an α-hydroxyamide (I), e.g. as described above.

Compounds (I) in which $R^a$ or $R^b$ represents a lower alkoxy group may, for example, be prepared by alkylation of a compound (I) in which $R^a$ or $R^b$ represents a hydroxy group, e.g. by reaction with a base such as an alkali metal hydride (e.g. potassium hydride) and an alkyl halide (e.g. the appropriate iodide). It will be appreciated that the 1α- and 3β-hydroxy groups of the starting material (I) should preferably be O-protected during such alkylations.

Compounds of general formulae (II), (IV) and (V) may themselves be prepared by any convenient method, e.g. as described in the above-mentioned WO 93/09093. One useful route to such compounds is from compounds of general formula (VI)

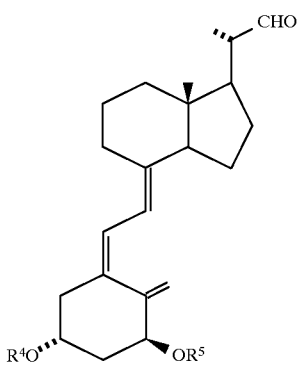

(VI)

(where $R^4$ and $R^5$ are as defined above) and/or 5,6-trans isomers thereof and the corresponding 1-deoxy compounds; such compounds may be obtained through oxidative cleavage (e.g. by ozonolysis) of the 22,23,-double bond of vitamin $D_2$, 1α-hydroxy vitamin $D_2$ or O-protected derivatives thereof, these preferably being stabilised by formation of a Diels Alder dienophile adduct, e.g. with sulphur dioxide or a diazacyclo compound, for example as described in GB-A-2114570 (the contents of which are incorporated herein by reference).

Such 20S compounds (VI), optionally still in the form of their dienophile adducts, may be isomerised by, for example, treatment with a mild base, e.g. an inorganic base such as sodium bicarbonate or a tertiary organic base such as 1,4-diazabicyclo[2.2.2]octane ("DABCO") or 1,8-diazabicyclo [5.4.0]undec-7-ene ("DBU"). This yields a mixture of 20R and 20S isomers from which the pure 20R epi-isomer may be isolated chromatographically; alternatively separation of a desired epi-isomer may be delayed until a later stage in the synthesis, up to and including the final step.

Higher homologues of compounds of general formula (VI) and corresponding epi-isomers, i.e. compounds containing an alkylene group Y in the 17-position side chain, may for example be obtained by reducing the aldehyde function, e.g. using a metal hydride reducing agent such as sodium borohydride, yielding a corresponding hydroxymethyl compound. This may be converted to a corresponding halomethyl compound, e.g. by conversion to a sulphonate ester such as a tosylate and nucleophilic displacement of the sulphonate group by reaction with a halide salt such as an alkali metal bromide, whereafter the halomethyl compound may be reacted with a metal cyanide or a metalated derivative of acetonitrile; the cyano group so introduced may be converted to a carboxaldehyde group by, for example, reaction with a metal hydride reducing agent such as diisobutyl aluminium hydride. This overall procedure may be repeated as needed to yield compounds containing a desired Y group.

In general O-protected compounds of formulae (II), (IV) and (V) in which A= represents a group (A-9) as hereinbefore defined may be subjected to 1α- hydroxylation as described under (B) above to give compounds in which A= represents a group (A-2) or (A-3) as hereinbefore defined in which $R^5$ represents hydrogen. Such compounds or protected derivatives thereof, e.g. in which $R_5$ is trimethylsilyl, may be hydrogenated (e.g. in the presence of a noble metal catalyst such as tris-triphenylphosphine rhodium chloride) to yield corresponding compounds in which A= represents a group (A-4) or (A-5) as hereinbefore defined, or may be cyclopropanated (e.g. by reaction with methylene iodide in the presence of zinc/copper couple) to yield corresponding compounds in which A= represents a group (A-6) or (A-7) as hereinbefore defined. Where appropriate, the compounds so obtained may be converted to compounds in which $R^5$ is an O-protecting group (e.g. by silylation).

19-Nor compounds, i.e. those in which A= represents a group (A-8) as hereinbefore defined, may be prepared as described by Perlman et al., Tetrahedron Letters (1992), 33, pp 2937–2940.

D) By reaction of a compound of formula (I) to modify the substitution pattern about the A= group, followed if necessary and/or desired by isomerisation and/or removal of protecting groups.

Thus for example, compounds (I) in which A= represents a group (A-4) or (A-5) may be prepared by hydrogenation of corresponding compounds in which A= represents (A-2) or (A-3), e.g. using the method of GB-A-1583749. It will be appreciated that such hydrogenation may alternatively be effected at an earlier stage of a reaction sequence, e.g. on a starting material or intermediate.

Compounds (I) in which A= represents a group (A-6) or (A-7) may be prepared from corresponding compounds in which A= represents (A-2) or (A-3) (in which $R^4$ is an O-protecting group and $R^5$ is a hydrogen atom or a trimethylsilyl group) by Simmons-Smith methylenation (see e.g. Neef et al., Tetrahedron Letters (1991), 32, pp 5073–5076).

Compounds (I) in which A= represents a group (A-8) may, for example, be prepared by cleavage of the 7,8-double bond of an appropriate vitamin D derivative (e.g. a precursor compound (I) in which A= is a group (A-9)), for example by ozonolysis or by successive reaction with potassium permanganate and sodium periodate, followed by Wittig-Horner reaction of the resulting 8-one with an appropriate ring A precursor, e.g. of formula (VII)

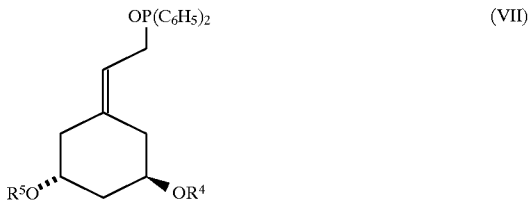

(VII)

(where $R^4$ and $R^5$ represent O-protecting groups)—see, for example, Perlman et al., Tetrahedron Letters (1992), 33, pp 2937–2940.

In general, either 5,6-cis or 5,6-trans geometry may be present at any of the various steps described in (C) and (D) above, although it may be preferred to employ 5,6-trans isomers in the above-mentioned 1α-hydroxylation and 22,23-double bond oxidative cleavage reactions. Conversion of 5,6-trans geometry to 5,6-cis is thus most advantageously effected after introduction of the 1α-hydroxyl group.

It will be appreciated that many of the reaction sequences described above may also be accomplished using appropriate steroid-5,7-dienes (or steroid-5-enes which are convertible into such dienes), followed by conversion of the steroid products into the desired vitamin D analogues, e.g. by irradiation with UV light.

In general, O-protecting groups present at the 1α-and/or 3β- positions and/or in the side chain may be removed by, for example, conventional methods such as are well documented in the literature. Thus esterifying acyl groups may be removed by basic hydrolysis, e.g. using an alkali metal alkoxide in an alkanol. Etherifying groups such as silyl groups may be removed by acid hydrolysis or treatment with a fluoride salt, e.g. a tetraalkylammonium fluoride. The use of such acid-labile but base-stable protecting groups may be of particular advantage during homologation steps to build up a desired side chain, in view of the strongly basic conditions normally employed for such reactions.

The following non-limitative examples serve to illustrate the invention. All temperatures are in EC. Where appropriate starting materials and intermediates are identified with reference to the following general formula (VIII)

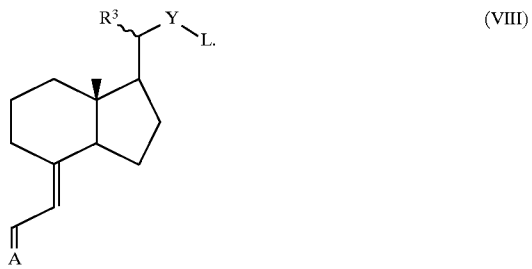

PREPARATION 1 a) 20α-Acetoxymethyl-1α-hydroxy-3β-triisopropylsilyloxy-9,10-secopregna-5(E), 7-diene [Formula (VIII)—A=(A-5), $R^3$=α-$CH_3$, $R^4$=(i-Pr)$_3$ Si, $R^5$=H, L=O.CO.$CH_3$, Y=$CH_2$]

A solution of tris-triphenylphosphine rhodium chloride (450 mg) in benzene (30 ml) (or in a 1:1 mixture of benzene and ethanol) is stirred under hydrogen until no further uptake is observed. A solution of 20α-acetoxymethyl-1α-hydroxy-3β-triisopropylsilyloxy-9,10-secopregna-5(E),7,10 (19)-triene [Formula (VIII)—A=(A-3), $R^3$=α-$CH_3$, $R^4$=(i-Pr)$_3$ Si, $R^5$=H, L=O.CO.$CH_3$, $Y^a$=$CH_2$—as an alternative the corresponding 1α-trimethylsilyl ether may be used] (500 mg) in benzene (30 ml) is added and the mixture stirred under hydrogen until 1 equivalent of hydrogen has been taken up (ca 21 ml). The title compounds are purified by chromatography [the 10(R) and 10(S) isomers may optionally be resolved at this stage] and have UV $\lambda_{max}$ ca. 243, 251 and 261 nm, with ε=ca. 35,000; 40,000 and 27,000 respectively.

b) 1α, 3β-Bis-triisopropylsilyloxy-20α-hydroxymethyl-9,10-secopregna-5(E), 7-diene [Formula (VIII)—A=(A-5), $R^3$=α-$CH_3$, $R^4$=$R^5$=(i-Pr)$_3$ Si, L=OH, Y=$CH_2$]

The diene from (a) above (ca 500 mg) in dichloromethane (2 ml) is treated with chlorotriisopropylsilane (250 mg) and imidazole (350 mg) and the mixture stirred overnight at room temperature. After work up the crude bis-silyl ether is dissolved in tetrahydrofuran (10 ml), treated with lithium aluminium hydride (100 mg) and stirred at room temperature for 1–2 hours. After decomposition of the excess lithium aluminium hydride (careful addition of saturated aqueous sodium sulphate) the reaction mixture is worked up to afford the title alcohol.

PREPARATION 2

1α,3β-Bis-triisopropylsilyloxy-20α(-hydroxymethyl-9,10-secopregna-5(Z),7-diene [Formula (VIII)—A=(A-4), $R^3$=α-$CH_3$, $R^4$=$R^5$=(i-Pr)$_3$ Si, L=OH, Y=$CH_2$]

The 5 (E)-triene starting material in Preparation 1(a) is photoisomerised in benzene in the presence of phenazine by irradiation for 1 hour, to yield the corresponding 5(Z)-triene. This product is hydrogenated as described in Preparation 1(a) and silylated and de-acetylated as described in Preparation 1(b) to give the title compound. UV $\lambda_{max}$ ca. 243, 251 and 261 nm with ε=ca. 35,000; 40,000 and 27,000 respectively.

The epi (i.e. 20β-hydroxymethyl) compounds corresponding to the products of Preparations 1 and 2 are prepared by the same procedures starting with the 20-epi compound 20β-acetoxymethyl-1α-hydroxy-3β-triisopropylsilyloxy-9,10-secopregna-5(E),7,10(19)-triene [Formula (VIII)—A=(A-3), $R^3$=β-$CH_3$, $R^4$=(i-Pr)$_3$ Si, $R^5$=H, L=O.CO.$CH_3$, Y=$CH_2$]. This is itself prepared by isomerisation of the 20-aldehyde obtained by ozonolysis of the sulphur dioxide adduct of vitamin $D_2$ followed by reduction and 1α-hydroxylation of the 20-epi aldehyde.

PREPARATION 3 a) 20α-Acetoxymethyl-1α-hydroxy-3β-triisopropylsilyloxy-10-spirocyclopropyl-9,10-secopregna-5(E),7-diene [Formula (VIII)—A=(A-7), $R^3$=α-$CH_3$, $R^4$=(i-Pr)$_3$ Si, $R^5$=H, L=O.CO.$CH_3$, Y=$CH_2$]

A mixture of zinc/copper couple (1.08 g) and diiodomethane (0.9 ml) in ether (6 ml) is heated under reflux with stirring for 40 minutes. A solution of 20α-acetoxymethyl-1α-hydroxy-3β-triisopropylsilyloxy-9,10-secopregna-5(E),7,10(19)-triene [Formula (VIII)—A=(A-3), $R^3$=α-$CH_3$, $R^4$=(i-Pr)$_3$ Si, $R^5$=H, L=O.CO.$CH_3$, Y=$CH_2$—as an alternative the corresponding 1α-trimethylsilyl ether may be used] (ca. 500 mg) in ether (9 ml) is added, and the mixture is stirred and heated under reflux until most of the starting material has disappeared (TLC control: usually about 4 hours for the 1α-trimethylsilyl ether, less for the 1α-hydroxy compound). The reaction mixture is filtered, the solvent removed and the product chromatographed to remove the remaining diiodomethane. The title compound has UV $\lambda_{max}$ ca. 246, 253 and 263 nm, with ε=ca. 29,000; 36,000 and 25,000 respectively.

b) 1α,3β-Bis-triisopropylsilyloxy-20α-hydroxymethyl-10-spirocyclopropyl-9,10-secopregna-5(E),7-diene [Formula (VIII)—A=(A-7), $R^3$=α-$CH_3$, $R^4$=$R^5$=(i-Pr)$_3$ Si, L=OH, Y=$CH_2$]

The diene from (a) above (ca. 500 mg) in dichloromethane (2 ml) is treated with chlorotriisopropylsilane (250 mg) and imidazole (350 mg) and the mixture stirred overnight at room temperature. After work up the crude bis-silyl ether is dissolved in tetrahydrofuran (10 ml), treated with lithium aluminium hydride (100 mg) and stirred at room temperature for 1–2 hours. After decomposition of the excess lithium aluminium hydride (careful addition of saturated aqueous sodium sulphate) the reaction mixture is worked up to afford the title alcohol.

PREPARATION 4

1α,3β-Bis-triisopropylsilyloxy-20α-hydroxymethyl-10-spirocyclopropyl-9,10-secopregna-5(Z),7-diene [Formula (VIII)—A=(A-6), $R^3$=α-$CH_3$, $R^4$=$R^5$=(i-Pr)$_3$ Si, L=OH, Y=$CH_2$]

The procedure of Preparation 3(a) is repeated starting from the corresponding 5(Z)-triene, prepared by photoisomerization of the 5(E)-triene as described in Preparation 2; the reaction of the 5(Z)-triene is somewhat slower than that of the 5(E)-triene. Silylation and de-acetylation as described in Preparation 3(b) gives the title compound. UV $\lambda_{max}$ ca. 246, 253 and 263 nm with ε=ca. 29,000; 36,000 and 25,000 respectively.

PREPARATION 5

1α,3β-Bis-t-butyldimethylsilyloxy-20β-hydroxymethyl-19-nor-9,10-secopregna-5(E),7-diene [Formula (VIII)—A=(A-8), $R^3$=β-$CH_3$, $R^4$=$R^5$=t-Bu(Me)$_2$Si, L=OH, Y=$CH_2$]

1α,3β-Bis-t-butyldimethylsilyloxy-20α-formyl-19-nor-9,10-secopregna-5,7-diene [Formula (II)—A=(A-8), $R^1$=α-$CH_3$, $R^4$=$R^5$=t-Bu(Me)$_2$Si, Y=valence bond] obtained as in Tetrahedron Lett. (1992), 33, p 2937, (about 1.5 g) is dissolved in benzene (15 ml) and methanol (15 ml) and isomerised by storage overnight with DBU (400 μl) at 0°. The mixture of normal (20α-formyl) and epi (20β-formyl) aldehydes may be resolved by chromatography (silica eluted with 15% benzene in hexane) before or after reduction of the aldehyde (ca 1 g) in benzene (30 ml) by dropwise treatment with sodium borohydride, (400 mg) in ethanol (15 ml) at 0°, whereafter the reaction mixture is stirred at 0° for a further 0.5 hour. After work up the product is resolved by chromatography (silica gel eluting with benzene or ether in hexane) to yield the title compound.

PREPARATION 6 a) 1α,3β-Bis-triisopropylsilyloxy-23-nor-9,10-secochola-5(E),7,10, 19-trienic acid, nitrile (mixture of 20-normal and 20- epi isomers) [Formula (VIII)—A=(A-3), $R^3$=α- and β-$CH_3$, $R^4$=$R^5$=(i-Pr)$_3$ Si, L=CN, Y=$CH_2$]

A solution of 1α,3β-bis-triisopropylsilyloxy-20(α,β)-tosyloxymethyl-9,10-secopregna-5(E),7,10(19)-triene [Formula (VIII)—A=(A-3), $R^3$=α,β-$CH_3$, $R^4$=$R^5$=(i-Pr)$_3$Si, L=O.tosyl, Y=$CH_2$] (1 g) in dimethylsulphoxide (5 ml) containing potassium cyanide (390 mg) was heated at 90° for 2 hours, and the product was extracted (diethyl ether), washed and purified by column chromatography to give the title nitrile (748 mg). UV (Et$_2$O) $\lambda_{max}$ 267, $\lambda_{man}$ 229 nm; NMR (CCl$_4$) δ 5.36–6.13 (ABq, 6,7-H's), 4.83 (bs, 19-H's), 4.13–4.46 (m, 1,3-H's), 0.53 (s, 18-H's).

b) 1α,3β-Bis-triisopropylsilyloxy-23-nor-9,10-secochola-5(E),7,10,19-trienic carboxaldehyde, (mixture of 20- normal and 20- epi isomers) [Formula (II)—A=(A-3), $R^3$=α- and β-$CH_3$, $R^4$=$R^5$=(i-Pr)$_3$ Si, Y=$CH_2$]

The nitrile from (a) above (480 mg) in hexane (3 ml) was cooled to −78° and treated with diisobutylaluminium hydride (1.4 ml of a 1M solution in heptane). The mixture was stirred at 0° for 1 hour, treated with ether and saturated ammonium chloride solution, and the product isolated by extraction into ether. The crude product had UV (Et$_2$O) $\lambda_{max}$ 270, $\lambda_{min}$ 229 nm; IR (CCl$_4$) $\lambda_{max}$ 1730 cm$^{-1}$; NMR (CCl$_4$) δ 10.6 (bs, CHO), 5.53–6.23 (ABq, 6,7-H's), 4.76 (bs, 19-H's), 4.16–4.43 (m, 1,3-H's), 0.56 (s, 18-H's).

c) 1α,3β-Bis-triisopropylsilyloxy-20(α,β)—(2-hydroxyethyl)-9,10-secopregna-5(E),7,10,19-triene [Formula (VIII)—A=(A-3), $R^3$=α- and β-$CH_3$, $R^4$=$R^5$=(i-Pr)$_3$ Si, L=OH, Y=(CH$_2$)$_2$]

The aldehyde from (b) above (440 mg) in benzene (10 ml) was treated at 0° with a solution of sodium borohydride (105 mg) in ethanol (10 ml) followed by stirring at room temperature for 45 minutes. After work up the product was purified by chromatography to give the title compound (380 mg), UV (Et$_2$O) $\lambda_{max}$ 269, $\lambda_{min}$ 228 nm; IR (CCl$_4$) $v_{max}$ 3500–3700 cm$^{-1}$; NMR (CCl$_4$) δ 5.53–6.3 (ABq, 6,7-H's), 4.73 (bs, 19-H's), 4.16–4.43 (m, 1,3-H's), 0.56 (s, 18-H's).

The isomers (at C-20) were resolved by careful chromatography of 1.2 g of mixture on silica gel developed with 30% benzene in hexane. The 20β-(epi) isomer (145 mg) was less polar and eluted first followed by a mixture of isomers and then the 20α-(normal) isomer (360 mg).

d) 1α,3β-Bis-triisopropylsilyloxy-20α-(2-bromoethyl)-9,10-secopregna-5(E),7,10(19)-triene [Formula (VIII)—A=(A-3), $R^3$=α-$CH_3$, $R^4$=$R^5$=(i-Pr)$_3$Si, L=Br, Y=(CH$_2$)$_2$]

The normal alcohol from (c) above (200 mg) was stirred at room temperature for 2 hours in dichloromethane (5 ml) containing p-toluenesulphonyl chloride (110 mg) and pyridine (243 μl). Sodium bicarbonate (20 ml of a saturated solution) was added, the stirring continued for a further 2 hours, and the reaction mixture worked up. The crude tosylate was dissolved in acetonitrile (6.6 ml) and dichloromethane (6.6 ml) containing lithium bromide (317 mg) and 1,8 bis-dimethylaminonaphthalene ("proton sponge" 40 mg) and the mixture heated under reflux at 80E for 30 minutes. The mixture was then cooled and worked up to give the title bromide (261 mg, purified by chromatography). UV (Et$_2$O) $\lambda_{max}$ 267, $\lambda_{min}$ 228 nm; NMR (CCl$_4$) δ 5.43–6.16 (ABq, 6,7-H's), 4.76 (bs, 19-H's), 4.14–4.45 (m, 1,3-H's), 3.16 (m, CH$_2$Br), 0.5 (s, 18-H's).

PREPARATION 7 a) 1α,3β-Bis-triisopropylsilyloxy-20α-formyl-9,10-secopregna-5(E),7-diene [Formula (II)—A=(A-5), $R^3$=α-$CH_3$, $R^4$=$R^5$=(i-Pr)$_3$Si, Y=valence bond]

The title compound is prepared by oxidation of the product from Preparation 1(b) using pyridinium dichromate, pyridinium chlorochromate or activated dimethylsulphoxide (Swern procedure).

b) 1α,3β-Bis-triisopropylsilyloxy-20α-formyl-9,10-secopregna-5(Z),7-diene [Formula (II)–A=(A-4), $R^3$=α-$CH_3$, $R^4$=$R^5$=(i-Pr)$_3$Si, Y=valence bond]

The title compound is prepared by similar oxidation of the product from Preparation 2.

c) 1α,3β-Bis-triisopropylsilyloxy-20α-formyl-10-spirocyclopropyl-9,10-secopregna-5(E),7-diene [Formula (II)—A=(A-7), $R^3$=α-$CH_3$, $R^4$=$R^5$=(i-Pr)$_3$Si, Y=valence bond]

The title compound is prepared by similar oxidation of the product from Preparation 3(b).

d) 1α,3β-Bis-triisopropylsilyloxy-20α-formyl-10-spirocyclopropyl-9,10-secopregna-5(Z),7-diene [Formula (II)—A=(A-6), $R^3$=α-$CH_3$, $R^4$=$R^5$=(i-Pr)$_3$Si, Y=valence bond]

The title compound is prepared by similar oxidation of the product from Preparation 4.

PREPARATION 8 a) 1α,3β-Bis-triisopropylsilyloxy-20α-formylmethyl-9,10-secopregna-5(E),7-diene [Formula (II)—A=(A-5), $R^3$=α-$CH_3$, $R^4$=$R^5$=(i-Pr)$_3$Si, Y=$CH_2$]

The title compound is prepared by reacting the product of Preparation 1(b) in accordance with the procedures of Preparations 6(a) and (b).

b) 1α,3β-Bis-triisopropylsilyloxy-20α-formylmethyl-9,10-secopregna-5(Z),7-diene [Formula (II)—A=(A-4), $R^3$=α-$CH_3$, $R^4$=$R^5$=(i-Pr)$_3$Si, Y=$CH_2$]

The title compound is prepared by similar reaction of the product from Preparation 2.

c) 1α,3β-Bis-triisopropylsilyloxy-20α-formylmethyl-10-spirocyclopropyl-9,10-secopregna-5(E),7-diene [Formula (II)—A=(A-7), $R^3$=α-$CH_3$, $R^4$=$R^5$=(i-Pr)$_3$Si, Y=$CH_2$]

The title compound is prepared by similar reaction of the product from Preparation 3(b).

d) 1α,3β-Bis-triisopropylsilyloxy-20α-formylmethyl-10-spirocyclopropyl-9,10-secopregna-5(Z),7-diene [Formula (II)—A=(A-6), $R^3$=α-$CH_3$, $R^4$=$R^5$=(i-Pr)$_3$Si, Y=$CH_2$]

The title compound is prepared by similar reaction of the product from Preparation 4.

e) 1α,3β-Bis-t-butyldimethylsilyloxy-20β-formylmethyl-19-nor-9,10-secopregna-5(E),7-diene [Formula (II)—A=(A-8), $R^3$=β-$CH_3$, $R^4$=$R^5$=t-Bu(Me)$_2$Si, Y=$CH_2$]

The title compound is prepared by similar reaction of the product from Preparation 5.

EXAMPLE 1 a) 1α,3β-Bis-triisopropylsilyloxy-23-hydroxy-9,10-secochola-5(E),7,10(19)-trien-24-oic acid piperidine amide, mixture of 20R and 20S isomers [Formula (I)—A=(A-3), $R^1+R^2=(CH_2)_5$, $R^3=\alpha$- and $\beta$-$CH_3$, $R^4=R^5=(i\text{-}Pr)_3Si$, $R^a=OH$, $R^b=H$, Y=valence bond]

Lithium diisopropylamide (0.5 ml of a 2.0M solution in heptane/tetrahydrofuran/ethylbenzene—Aldrich, catalogue no. 36, 179-8) was added dropwise to a solution of a mixture of the 20R and 20S isomers of 1α,3β-bis-triisopropylsilyloxy-9,10-secochola-5(E),7,10(19)-trien-24-oic acid piperidine amide [Formula (IV)—A=(A-3), $R^1+R^2=(CH_2)_5$, $R^3=\alpha$- and $\beta$-$CH_3$, $R^4=R^5=(i\text{-}Pr)_3Si$, Y=valence bond] (90 mg) and triphenylphosphine (63 mg) in tetrahydrofuran (1.5 ml) and the resulting mixture was stirred for 1 hour at room temperature. The solution was added dropwise to diethyl ether (2 ml) and oxygen was passed through for 1 hour. The reaction mixture was quenched with saturated aqueous ammonium chloride, the product was extracted into diethyl ether, worked up and isolated by chromatography to give the title compound (30 mg) as an approximately 1:1 mixture of 23R and 23S isomers. UV ($Et_2O$) $\lambda_{max}$ 204, 269, $\lambda_{min}$ 229 nm, $E_{max}/E_{min}$ 3.9; IR ($CDCl_3$) $v_{max}$ 3520–3240 (OH), 1625, 1460 $cm^{-1}$.

b) 1α,3β-Bis-triisopropylsilyloxy-23-hydroxy-9,10-secochola-5(Z),7,10(19)-trien-24-oic acid piperidine amide, mixture of 20R and 20S isomers [Formula (I)—A=(A-2), $R^1+R^2=(CH_2)_5$, $R^3=\alpha$- and $\beta$-$CH_3$, $R^4=R^5=(i\text{-}Pr)_3Si$, $R^a=OH$, $R^b=H$, Y=valence bond]

A solution of the product from (a) above (30 mg) in benzene (4 ml) containing phenazine (14 mg) was photoisomerised by irradiation for 20 minutes. The product was worked up and isolated by chromatography to give the title compound (25 mg). UV ($Et_2O$) $\lambda_{max}$ 206, 261, $\lambda_{min}$ 228 nm, $E_{max}/E_{min}$ 1.8.

c) 1α,3β,23-Trihydroxy-9,10-secochola-5(Z),7,10(19)-trien-24-oic acid piperidine amide, mixture of 20R and 20S isomers [Formula (I)—A=(A-2), $R^1+R^2=(CH_2)_5$, $R^3=\alpha$- and $\beta$-$CH_3$, $R^4=R^5=R^b=H$, $R^a=OH$, Y=valence bond]

The product from (b) above (25 mg) in tetrahydrofuran (0.2 ml) was treated with tetrabutylammonium fluoride (0.2 ml of a 1M solution in tetrahydrofuran) at room temperature. After 3 hours the reaction mixture was worked up and the desilylated title compound (16 mg) was isolated by chromatography. UV (EtOH) $\lambda_{max}$ 207, 262, $\lambda_{min}$ 228 nm, $E_{max}/E_{min}$ 1.7; IR ($CDCl_3$) $v_{max}$ 3620–3300 (OH), 1630, 1460 $cm^{-1}$; NMR ($CDCl_3$) δ 0.57 (s, 18-H's), 3.0–3.7 (m, $NCH_2$'s), 3.9–4.6 (m, 1,3,23-H's), 4.8, 5.4 (ea. s, 19-H's), 5.6–6.5 (ABq, 6,7-H's).

The compound 1α,3β-trihydroxy-9,10-secochola-5(Z),7,10(19)-trien-24-oic acid diisopropylamide [Formula (I)—A=(A-2), $R^1=R^2=i\text{-}Pr$, $R^3=\alpha\text{-}CH_3$, $R^4=R^5=R^b=H$, $R^a=OH$, Y=valence bond] may be prepared by similar reaction according to steps (a) and (c) above starting from 1α,3β-bis-triisopropylsilyloxy-9,10-secochola-5(Z),7,10(19)-trien-24-oic acid diisopropylamide [Formula (I)—A=(A-2), $R^1=R^2=i\text{-}Pr$, $R^3=\alpha\text{-}CH_3$, $R^4=R^5=(i\text{-}Pr)_3Si$, $R^a=R^b=H$, Y=valence bond].

The compound 1α,3β,23-trihydroxy-9,10-secochola-5(Z),7,10(19)-trien-24-oic acid diethylamide [Formula (I)—A=(A-2), $R^1=R^2=C_2H_5$, $R^3=\alpha\text{-}CH_3$, $R^4=R^5=R^b=H$, $R^a=OH$, Y=valence bond] may be prepared by similar reaction according to steps (a) and (c) above starting from 1α,3β-bis-triisopropylsilyloxy-9,10-secochola-5(Z),7,10(19)-trien-24-oic acid diethylamide [Formula (I)—A=(A-2), $R^1=R^2=C_2H_5$, $R^3=\alpha\text{-}CH_3$, $R^4=R^5=(i\text{-}Pr)_3Si$, $R^a=R^b=H$, Y=valence bond].

The compound 1α,3β,23-trihydroxy-9,10-secochola-5(Z),7,10(19)-trien-24-oic acid morpholine amide [Formula (I)—A=(A-2), $R^1+R^2=(CH_2)_2O(CH_2)_2$, $R^3=\alpha\text{-}CH_3$, $R^4=R^5=R^b=H$, $R^a=OH$, Y=valence bond] may be prepared by similar reaction according to steps (a)–(c) above starting from 1α,3β-bis-triisopropylsilyloxy-9,10-secochola-5(E),7,10(19)-trien-24-oic acid morpholine amide [Formula (I)—A=(A-3), $R^1+R^2=(CH_2)_2O(CH_2)_2$, $R^3=\alpha\text{-}CH_3$, $R^4=R^5=(i\text{-}Pr)_3Si$, $R^a=R^b=H$, Y=valence bond].

The compound 1α,3β,23-trihydroxy-9,10-secochola-5(Z),7-dien-24-oic acid piperidine amide [Formula (I)—A=(A-4), $R^1+R^2=(CH_2)_5$, $R^3=\alpha\text{-}CH_3$, $R^4=R^5=R^b=H$, $R^a=OH$, Y=valence bond] may be prepared by similar reaction according to steps (a) and (c) above starting from 1α,3β-bis-triisopropylsilyloxy-9,10-secochola-5(Z),7-dien-24-oic acid piperidine amide [Formula (I)—A=(A-4), $R^1+R^2=(CH_2)_5$, $R^3=\alpha\text{-}CH_3$, $R^4=R^5=(i\text{-}Pr)_3Si$, $R^a=R^b=H$, Y=valence bond].

The compound 1α,3β,23-trihydroxy-10-spirocyclopropyl-9,10-secochola-5(Z),7-dien-24-oic acid piperidine amide [Formula (I)—A=(A-6), $R^1+R^2=(CH_2)_5$, $R^3=\beta\text{-}CH_3$, $R^4=R^5=R^b=H$, $R^a=OH$, Y=valence bond] may be prepared by similar reaction according to steps (a) and (c) above starting from 1α,3β-bis-triisopropy8lsilyloxy-10-spirocyclopropyl-9,10-secochola-5(Z),7-dien-24-oic acid piperidine amide [Formula (I)—A=(A-6), $R^1+R^2=(CH_2)_5$, $R^3=\alpha\text{-}CH_3$, $R^4=R^5=(i\text{-}Pr)_3Si$, $R^a=R^b=H$, Y=valence bond].

The compound 1α,3β,23b-trihydroxy-23-bis-homo-9,10-secochola-5(Z),7,10(19)-trien-24-oic acid dimethylamide [Formula (I)—A=(A-2), $R^1=R^2=CH_3$, $R^3=\alpha\text{-}CH_3$, $R^4=R^5=R^b=H$, $R^a=OH$, Y=$(CH_2)_2$] may be prepared by similar reaction according to steps (a) and (c) above starting from 1α,3β-bis-triisopropylsilyloxy-23-bis-homo-9,10-secochola-5(Z),7,10(19)-trien-24-oic acid dimethylamide [Formula (I)—A=(A-2), $R^1=R^2=CH_3$, $R^3=\alpha\text{-}CH_3$, $R^4=R^5=(i\text{-}Pr)_3Si$, $R^a=R^b=H$, Y=$(CH_2)_2$].

The compound 1α,3β,23-trihydroxy-19-nor-9,10-secochola-5,7-dien-24-oic acid piperidine amide [Formula (I)—A=(A-8), $R^1+R^2=(CH_2)_5$, $R^3=\alpha\text{-}CH_3$, $R^4=R^5=R^b=H$, $R^a=OH$, Y=valence bond] may be prepared by similar reaction according to steps (a) and (c) above starting from 1α,3β-bis-t-butyldimethylsilyloxy-19-nor-9,10-secochola-5,7-dien-24-oic acid piperidine amide [Formula (I)—A=(A-8), $R^1+R^2(CH_2)_5$, $R^3=\alpha\text{-}CH_3$, $R^4=R^5=t\text{-}Bu(Me)_2Si$, $R^a=R^b=H$, Y=valence bond].

The compound 1α,3β,23a-trihydroxy-23-homo-9,10-secochola-5(Z),7,10(19)-trien-24-oic acid piperidine amide [Formula (I)—A=(A-2), $R^1+R^2=(CH_2)_5$, $R^3=\alpha\text{-}CH_3$, $R^4=R^5=R^b=H$, $R^a=OH$, Y=$CH_2$] may be prepared by similar reaction according to steps (a)–(c) above starting from 1α,3β-bis-triisopropylsilyloxy-23-homo-9,10-secochola-5(E),7,10(19)-trien-24-oic acid piperidine amide [Formula (I)—A=(A-2), $R^1+R^2=(CH_2)_5$, $R^3=\alpha\text{-}CH_3$, $R^4=R^5=(i\text{-}Pr)_3Si$, $R^a=R^b=H$, Y=$CH_2$].

EXAMPLE 2 a) 1α,3β-Bis-triisopropylsilyloxy-20-epi-23-hydroxy-9,10-secochola-5(E),7,10(19)-trien-24-oic acid piperidine amide, [Formula (I)—A=(A-3), $R^1+R^2=(CH_2)_5$, $R^3=\beta\text{-}CH_3$, $R^4=R^5=(i\text{-}Pr)_3Si$, $R^a=OH$, $R^b=H$, Y=valence bond].

Lithium diisopropylamide (0.2 ml of a 2.0M solution in heptane/tetrahydrofuran/ethylbenzene) was added dropwise to a solution of 1α,3β-bis-triisopropylsilyloxy-20-epi-9,10-secochola-5(E),7,10(19)-trien-24-oic acid piperidine amide [Formula (IV)—A=(A-3), $R^1+R^2=(CH_2)_5$, $R^3=\beta\text{-}CH_3$, $R^4=R^5=(i\text{-}Pr)_3Si$, Y=valence bond] (160 mg) and triphenylphosphine (105 mg) in tetrahydrofuran (2 ml) and the resulting mixture was stirred for 1 hour at room temperature. The solution was added dropwise to diethyl ether (1 ml) and oxygen was passed through for 10 minutes. The reaction mixture was quenched with saturated aqueous ammonium chloride, the product was extracted into diethyl ether, worked up and isolated by chromatography to afford unreacted starting material (20 mg) and the title compound (110 mg) as an approximately 1:1 mixture of 23R and 23S isomers. UV (Et$_2$O) $\lambda_{max}$ 269, $\lambda_{min}$ 229 nm, $E_{max}/E_{min}$ 4.6; IR (CCl$_4$) $\nu_{max}$ 3520–3300 (OH), 1640, 1460 cm$^{-1}$; NMR (CCl$_4$) δ 0.57 (s, 18-H's), 3.0–3.7 (m, NCH$_2$'s), 3.8–4.6 (m, 1,3,23-H's), 4.6–5.4 (bs, 19-H's), 5.3–6.4 (ABq, 6,7-H's).

b) 1α,3β-Bis-triisopropylsilyloxy-20-epi-23-hydroxy-9,10-secochola-5(Z),7,10(19)-trien-24-oic acid piperidine amide [Formula (I)—A=(A-2), $R^1+R^2=(CH_2)_5$, $R^3=\beta\text{-}CH_3$, $R^4=R^5=(i\text{-}Pr)_3Si$, $R^a=OH$, $R^b=H$, Y=valence bond]

A solution of the product from (a) above (110 mg) in benzene (14 ml) containing phenazine (50 mg) was photoisomerised by irradiation for 45 minutes. The product was worked up and isolated by chromatography to give the title compound (70 mg). UV (Et$_2$O) $\lambda_{max}$ 205, 262, $\lambda_{min}$ 227 nm, $E_{max}/E_{min}$ 1.6; IR (CCl$_4$) $\nu_{max}$ 3520–3300 (OH), 1640, 1460 cm$^{-1}$; NMR (CCl$_4$) δ 0.5 (s, 18-H's), 3.0–3.6 (m, NCH$_2$'s), 3.6–4.5 (m, 1,3,23-H's), 4.5, 5.2 (bs, 19-H's), 5.4–6.1 (ABq, 6,7-H's).

c) 20-Epi-1α,3β,23-trihydroxy-9,10-secochola-5(Z),7,10(19)-trien-24-oic acid piperidine amide [Formula (I)—A=(A-2), $R^1+R^2=(CH_2)_5$, $R^3=\beta\text{-}CH_3$, $R^4=R^5=R^b=H$, $R^a=OH$, Y=valence bond]

The product from (b) above (70 mg) in tetrahydrofuran (0.5 ml) was treated with tetrabutylammonium fluoride (0.5 ml of a 1M solution in tetrahydrofuran) at room temperature. After 4 hours the reaction mixture was worked up and the desilylated title compound (16 mg) was isolated by chromatography. UV (EtOH) $\lambda_{max}$ 207, 263, $\lambda_{min}$ 227 nm, $E_{max}/E_{min}$ 1.6; IR (CDCl$_3$) $\nu_{max}$ 3640–3200 (OH), 1625 cm$^{-1}$; NMR (CDCl$_3$) δ 0.57 (s, 18-H's), 0.97 (d, 21-H's), 3.0–3.8 (m, NCH$_2$'s), 3.8–4.6 (m, 1,3,23-H's), 4.8, 5.4 (ea. s, 19-H's), 5.7–6.6 (ABq, 6,7-H's).

The compound 1α,3β,23-trihydroxy-20-epi-9,10-secochola-5(Z),7,10(19)-trien-24-oic acid diisopropylamide [Formula (I)—A=(A-2), $R^1=R^2=i\text{-}Pr$, $R^3=\beta\text{-}CH_3$, $R^4=R^5=R^b=H$, $R^a=OH$, Y=valence bond] may be prepared by similar reaction according to steps (a) and (c) above starting from 1α,3β-bis-triisopropylsilyloxy-20-epi-9,10-secochola-5(Z),7,10(19)-trien-24-oic acid diisopropylamide [Formula (I)—A=(A-2), $R^1=R^2=i\text{-}Pr$, $R^3=\beta\text{-}CH_3$, $R^4=R^5=(i\text{-}Pr)_3Si$, $R^a=R^b=H$, Y=valence bond].

The compound 1α,3β,23-trihydroxy-20-epi-9,10-secochola-5(Z),7,10(19)-trien-24-oic acid diethylamide [Formula (I)—A=(A-2), $R^1=R^2=C_2H_5$, $R^3=\beta\text{-}CH_3$, $R^4=R^5=R^b=H$, $R^a=OH$, Y=valence bond] may be prepared by similar reaction according to steps (a) and (c) above starting from 1α,3β-bis-triisopropylsilyloxy-20-epi-9,10-secochola-5(Z),7,10(19)-trien-24-oic acid diethylamide [Formula (I)—A=(A-2), $R^1=R^2=C_2H_5$, $R^3=\beta\text{-}CH_3$, $R^4=R^5=(i\text{-}Pr)_3Si$, $R^a=R^b=H$, Y=valence bond].

The compound 1α,3β,23a-trihydroxy-20-epi-9,10-secochola-5(Z),7,10(19)-trien-24-oic acid morpholine amide [Formula (I)—A=(A-2), $R^1+R^2=(CH_2)_2O(CH_2)_2$, $R^3=\beta\text{-}CH_3$, $R^4=R^5=R^bH$, $R^a=OH$, Y=valence bond] may be prepared by similar reaction according to steps (a)–(c) above starting from 1α,3β-bis-triisopropylsilyloxy-20-epi-9,10-secochola-5(E),7,10(19)-trien-24-oic acid morpholine amide [Formula (I)—A=(A-3), $R^1+R^2=(CH_2)_2O(CH_2)_2$, $R^3=\beta\text{-}CH_3$, $R^4=R^5=(i\text{-}Pr)_3Si$, $R^a=R^b=H$, Y=valence bond].

The compound 1α,3β,23a-trihydroxy-20-epi-23-homo-9,10-secochola-5(Z),7,10(19)-trien-24-oic acid piperidine amide [Formula (I)—A=(A-2), $R^1+R^2=(CH_2)_5$, $R^3=\beta\text{-}CH_3$, $R^4=R^5=R^b=H$, $R^a=OH$, Y=CH$_2$] may be prepared by similar reaction according to steps (a)–(c) above starting from 1α,3β-bis-triisopropylsilyloxy-20-epi-23-homo-9,10-secochola-5(E),7,10(19)-trien-24-oic acid piperidine amide [Formula (I)—A=(A-2), $R^1+R^2=(CH_2)_5$, $R^3=\beta\text{-}CH_3$, $R^4=R^5=(i\text{-}Pr)_3Si$, $R^a=R^b=H$, Y=CH$_2$].

The compound 1α,3β,23-trihydroxy-20-epi-19-nor-9,10-secochola-5,7-dien-24-oic acid piperidine amide [Formula (I)—A=(A-8), $R^1+R^2=(CH_2)_5$, $R^3=\beta\text{-}CH_3$, $R^4=R^5=R^b=H$, $R^a=OH$, Y=valence bond] may be prepared by similar reaction according to steps (a) and (c) above starting from 1α,3β-bis-t-butyldimethylsilyloxy-20-epi-19-nor-9,10-secochola-5,7-dien-24-oic acid piperidine amide [Formula (I)—A=(A-8), $R^1+R^2=(CH_2)_5$, $R^3=\beta\text{-}CH_3$, $R^4=R^5=t\text{-}Bu(Me)_2Si$, $R^a=R^b=H$, Y=valence bond].

EXAMPLE 3 a) 1α,3β-Bis-triisopropylsilyloxy-22-hydroxy-9,10-secochola-5(E),7,10(19)-trien-24-oic acid piperidine amide [Formula (I)—A=(A-3), $R^1+R^2=(CH_2)_5$, $R^3=\alpha\text{-}CH_3$, $R^4=R^5=(i\text{-}Pr)_3Si$, $R^a=H$, $R^b=OH$, Y=valence bond]

A solution of N-acetylpiperidine (305 mg) in tetrahydrofuran (5 ml) was treated with lithium diisopropylamide (1 ml of a 2M solution in tetrahydrofuran, added dropwise), stirred for 1 hour at room temperature and then cooled to −78E, whereafter a solution of 1α,3β-bis-triisopropylsilyloxy-20S-formyl-9,10-secopregna-5(E),7,10(19)-triene [Formula (II)—A=(A-3), $R^3=\alpha\text{-}CH_3$, $R^4=R^5=(i\text{-}Pr)_3Si$, Y=valence bond] (333 mg) in tetrahydrofuran (5 ml) was added dropwise. The resulting mixture was allowed to warm to room temperature, quenched with saturated aqueous ammonium chloride, and the product was extracted into ethyl acetate and purified by chromatography on silica gel (eluting with ethyl acetate in hexane) to give, in order of elution:

unreacted starting material (75 mg);

the less polar isomer of the title compound (100 mg), UV (Et$_2$O) $\lambda_{max}$ 269, $\lambda_{min}$ 234 nm, $E_{max}/E_{min}$ 3.0; IR (CCl$_4$) $\nu_{max}$ 3620–3300 (OH), 1630, 1465 cm$^{-1}$; NMR (CCl$_4$) δ 0.6 (s, 18-H's), 3.1–3.8 (m, NCH$_2$'S), 3.8–4.8 (m, 1,3,22-H's), 4.8–5.1 (bs, 19-H's), 5.6–6.6 (ABq, 6,7-H's); and the more polar isomer of the title compound (160 mg), UV (Et$_2$O) $\lambda_{max}$ 269, $\lambda_{min}$ 231 nm, $E_{max}/E_{min}$ 3.3; IR (CCl$_4$) $\nu_{max}$ 3620–3300 (OH), 1630, 1465 cm$^{-1}$; NMR (CDCl$_3$) δ 0.53 (s, 18-H's), 3.0–3.7 (m, NCH$_2$'s), 3.7–4.7 (m, 1,3,22-H's), 4.7–5.0 (bs, 19-H's), 5.4–6.6 (ABq, 6,7-H's).

b) 1α,3β-Bis-triisopropylsilyloxy-22-hydroxy-9,10-secochola-5(Z),7,10(19)-trien-24-oic acid piperidine amide (Isomer A) [Formula (I)—A=(A-2), $R^1+R^2=(CH_2)_5$, $R^3=\alpha\text{-}CH_3$, $R^4=R^5=(i\text{-}Pr)_3Si$, $R^a=H$, $R^b=OH$, Y=valence bond]

A solution of the less polar isomer from (a) above (50 mg) in benzene (6.5 ml) containing phenazine (22 mg) was photoisomerised by irradiation for 30 minutes. The product was worked up and isolated by chromatography to give the title compound (35 mg). UV (Et$_2$O) $\lambda_{max}$ 262, $\lambda_{min}$ 227 nm, $E_{max}/E_{min}$ 1.6; IR (CDCl$_3$) $\nu_{max}$ 3600–3200 (OH), 1610, 1450 cm$^{-1}$; NMR (CDCl$_3$) δ 0.53 (s, 18-H's), 3.0–3.7 (m, NCH$_2$'s), 3.7–4.7 (m, 1,3,22-H's), 4.8–5.2 (ea. s, 19-H's), 5.5–6.4 (ABq, 6,7-H's).

c) 1α,3β-Bis-triisopropylsilyloxy-22-hydroxy-9,10-secochola-5(Z),7,10(19)-trien-24-oic acid piperidine amide (Isomer B) [Formula (I)—A=(A-2), R$^1$+R$^2$=(CH$_2$)$_5$, R$^3$=α-CH$_3$, R$^4$=R$^5$=(i-Pr)$_3$Si, R$^a$=H, R$^b$=OH, Y=valence bond]

A solution of the more polar isomer from (a) above (70 mg) in benzene (9 ml) containing phenazine (32 mg) was photoisomerised by irradiation for 45 minutes. The product was worked up and isolated by chromatography to give the title compound (60 mg). UV (Et$_2$O) λ$_{max}$ 262, λ$_{min}$ 226 nm, E$_{max}$/E$_{min}$ 1.5; IR (CDCl$_3$) ν$_{max}$ 3640–3200 (OH), 1615, 1445 cm$^{-1}$; NMR (CDCl$_3$) δ 0.5 (s, 18-H's), 3.0–3.6 (m, NCH$_2$'s), 3.6–4.5 (m, 1,3,22-H's), 4.6–5.2 (ea. s, 19-H's), 5.5–6.4 (ABq, 6,7-H's).

d) 1α,3β,22-Trihydroxy-9,10-secochola-5(Z),7,10(19)-trien-24-oic acid piperidine amide (Isomer A) [Formula (I)—A=(A-2), R$^1$+R$^2$=(CH$_2$)$_5$, R$^3$=α-CH$_3$, R$^4$=R$^5$=R$^a$=H, R$^b$=OH, Y=valence bond]

The product from (b) above (35 mg) in tetrahydrofuran (0.3 ml) was treated with tetrabutylammonium fluoride (0.3 ml of a 1M solution in tetrahydrofuran) at room temperature. After 3 hours the reaction mixture was worked up and the desilylated title compound (20 mg) was isolated by thin layer chromatography. UV (Et$_2$O) λ$_{max}$ 263, λ$_{min}$ 227 nm, E$_{max}$/E$_{min}$ 1.6; IR (CDCl$_3$) ν$_{max}$ 3640–3240 (OH), 1615, 1450 cm$^{-1}$; NMR (CDCl$_3$) δ 0.6 (s, 18-H's), 0.95 (d, 21-H's), 3.0–3.7 (m, NCH$_2$'s), 3.8–4.6 (m, 1,3,22-H's), 4.8–5.4 (ea. s, 19-H's), 5.6–6.5 (ABq, 6,7-H's).

e) 1α,3β,22-Trihydroxy-9,10-secochola-5(Z),7,10(19)-trien-24-oic acid piperidine amide (Isomer B) [Formula (I)—A=(A-2), R$^1$+R$^2$=(CH$_2$)$_5$, R$^3$=α-CH$_3$, R$^4$=R$^5$=R$^a$=H, R$^b$=OH, Y=valence bond]

The product from (c) above (60 mg) in tetrahydrofuran (0.5 ml) was treated with tetrabutylammonium fluoride (0.5 ml of a 1M solution in tetrahydrofuran) at room temperature. After 3 hours the reaction mixture was worked up and the desilylated title compound (24 mg) was isolated by thin layer chromatography. UV (EtOH) λ$_{max}$ 263, λ$_{min}$ 227 nm, E$_{max}$/E$_{min}$ 1.6; IR (CDCl$_3$) ν$_{max}$ 3640–3160 (OH), 1615, 1445 cm$^{-1}$; NMR (CDCl$_3$) δ 0.5 (s, 18-H's), 3.0–3.6 (m, NCH$_2$'s), 3.6–4.4 (m, 1,3,22-H's), 4.5–5.2 (ea. s, 19-H's), 5.5–6.4 (ABq, 6,7-H's).

f) 1α,3β-Bis-triisopropylsilyloxy-22-hydroxy-9,10-secochola-5(E),7,10(19)-trien-24-oic acid diisopropylamide [Formula (I)—A=(A-3), R$^1$=R$^2$=i-Pr, R$^3$=α-CH$_3$, R$^4$=R$^5$=(i-Pr)$_3$Si, R$^a$=H, R$^b$=OH, Y=valence bond]

A solution of N,N-diisopropylacetamide (515 mg) in tetrahydrofuran (13.5 ml) was treated with lithium diisopropylamide (1.5 ml of a 2M solution in tetrahydrofuran, added dropwise), stirred for 1.5 hours at room temperature and then cooled to −78E. A solution of 1α,3β-bis-triisopropylsilyloxy-20S-formyl-9,10-secopregna-5(E),7,10 (19)-triene [Formula (II)—A=(A-3), R$^3$=α-CH$_3$, R$^4$=R$^5$=(i-Pr)$_3$Si, Y=valence bond] (100 mg) in tetrahydrofuran (2 ml) was treated at −78E with a portion of the thus-obtained enolate solution (3.8 ml, added dropwise). The temperature was maintained at −78E for 1 hour, whereafter the reaction mixture was quenched with saturated aqueous ammonium chloride, and the product was extracted into ethyl acetate and purified by chromatography to give (A) the less polar isomer of the title compound (38 mg): UV (Et$_2$O) λ$_{max}$ 268 nm; IR (CCl$_4$) ν$_{max}$ 3600–3300 (OH), 1635 cm$^{-1}$; NMR (CCl$_4$) δ 0.6 (s, 18-H's), 3.3–4.0 (m, NCH's), 4.0–4.8 (m, 1,3,22-H's), 4.8–5.0 (bs, 19-H's), 5.4–6.4 (ABq, 6,7's) and (B) the more polar isomer (48 mg): UV (Et$_2$O) λmax 269 nm; IR (CCl$_4$) ν$_{max}$ 3600–3200 (OH), 1630, 1470 cm$^{-1}$; NMR (CDCl$_3$) δ 0.53 (s, 18-H's), 3.2–3.7 (m, NCH's), 3.7–4.7 (m, 1,3,22-H's), 4.7–5.1 (bs, 19-H's), 5.5–6.5 (ABq, 6,7-H's).

g) 1α,3β-Bis-triisopropylsilyloxy-22-hydroxy-9,10-secochola-5(Z),7,10(19)-trien-24-oic acid diisopropylamide (Isomer A) [Formula (I)—A=(A-2), R$^1$=R$^2$=i-Pr, R$^3$=α-CH$_3$, R$^4$=R$^5$=(i-Pr)$_3$Si, R$^a$=H, R$^b$=OH, Y=valence bond]

A solution of the less polar isomer from (f) above (38 mg) in benzene (5 ml) containing phenazine (17 mg) was photoisomerised by irradiation for 1 hour. The product was worked up and isolated by chromatography to give the title compound (30 mg). UV (Et$_2$O) λ$_{max}$ 263, λ$_{min}$ 226 nm, E$_{max}$/E$_{min}$ 2.1; IR (CCl$_4$) ν$_{max}$ 3600–3200 (OH), 1635, 1470 cm$^{-1}$; NMR (CCl$_4$) δ 0.56 (s, 18-H's), 3.3–4.6 (m, NCH's, 1,3,22-H's), 4.6–5.3 (ea. s, 19-H's), 5.5–6.3 (ABq, 6,7-H's).

h) 1α,3β-Bis-triisopropylsilyloxy-22-hydroxy-9,10-secochola-5(Z),7,10(19)-trien-24-oic acid diisopropylamide (Isomer B) [Formula (I)—A=(A-2), R$^1$=R$^2$=i-Pr, R$^3$=α-CH$_3$, R$^4$=R$^5$=(i-Pr)$_3$Si, R$^a$=H, R$^b$=OH, Y=valence bond]

A solution of the more polar isomer from (f) above (48 mg) in benzene (6 ml) containing phenazine (22 mg) was photoisomerised by irradiation for 1 hour. The product was worked up and isolated by chromatography to give the title compound (30 mg). UV (Et$_2$O)λ$_{max}$ 264, λ$_{min}$ 226 nm, E$_{max}$/E$_{min}$ 2.0; IR (CCl$_4$) ν$_{max}$ 3600–3200 (OH), 1630, 1465 cm$^{-1}$; NMR (CCl$_4$) δ 0.5 (s, 18-H's), 3.2–4.6 (m, NCH's, 1,3,22-H's), 4.7–5.2 (ea. s, 19-H's), 5.5–6.3 (ABq, 6,7-H's).

i) 1α,3β,22-Trihydroxy-9,10-secochola-5(Z),7,10(19)-trien-24-oic acid diisopropylamide (Isomer A) [Formula (I)—A=(A-2), R$^1$=R$^2$=i-Pr, R$^3$=α-CH$_3$, R$^4$=R$^5$=R$^a$=H, R$^b$=OH, Y=valence bond]

The product from (g) above (30 mg) in tetrahydrofuran (0.23 ml) was treated with tetrabutylammonium fluoride (0.23 ml of a 1M solution in tetrahydrofuran) at room temperature. After 4 hours the reaction mixture was worked up and the desilylated title compound (14 mg) was isolated by thin layer chromatography. UV (EtOH) λ$_{max}$ 265, λ$_{min}$ 227 nm, E$_{max}$/E$_{min}$ 2.0; IR (CDCl$_3$) ν$_{max}$ 3640–3200 (OH), 1620, 1450 cm$^{-1}$; NMR (CDCl$_3$) δ 0.57 (s, 18-H's), 0.93 (d, 21-H's), 3.5–4.6 (m, NCH's, 1,3,22-H's), 4.7–5.4 (ea. s, 19-H's), 5.7–6.6 (ABq, 6,7-H's).

j) 1α,3β,22-Trihydroxy-9,10-secochola-5(Z),7,10(19)-trien-24-oic acid diisopropylamide (Isomer B) [Formula (I)—A=(A-2), R$^1$=R$^2$=i-Pr, R$^3$=α-CH$_3$, R$^4$R$^5$=R$^a$=H, R$^b$=OH, Y=valence bond]

The product from (h) above (38 mg) in tetrahydrofuran (0.285 ml) was treated with tetrabutylammonium fluoride (0.285 ml of a 1M solution in tetrahydrofuran) at room temperature. After 3 hours the reaction mixture was worked up and the desilylated title compound (21 mg) was isolated by thin layer chromatography. UV (EtOH) λ$_{max}$ 265, λ$_{min}$ 227 nm, E$_{max}$/E$_{min}$ 2.0; IR (CDCl$_3$) ν$_{max}$ 3640–3220 (OH), 1620, 1455 cm$^{-1}$; NMR (CDCl$_3$) δ 0.53 (s, 18-H's), 3.6–4.7 (m, NCH's 1,3,22-H's), 4.8–5.4 (ea. s, 19-H's), 5.7–6.6 (ABq, 6,7-H's).

The compound 1α,3β,22-trihydroxy-9,10-secochola-5(Z),7,10(19)-trien-24-oic acid dimethylamide [Formula (I)—A=(A-2), R$^1$=R$^2$=CH$_3$, R$^3$=α-CH$_3$, R$^4$=R$^5$=R$^a$=H, R$^b$=OH, Y=valence bond] may similarly be prepared by repeating the above procedures using N,N-dimethylacetamide as amide in place of the N-acetylpiperidine used in step (a) or the N,N-diisopropylacetamide used in step (f).

The compound 1α,3β,22-trihydroxy-9,10-secochola-5(Z),7,10(19)-trien-24-oic acid morpholine amide [Formula (I)—A=(A-2), R$^1$+R$^2$=(CH$_2$)$_2$O(CH$_2$)$_2$, R$^3$=α-CH$_3$, R$^4$=R$^5$=R$^a$=H, R$^b$=OH, Y=valence bond] may similarly be prepared by repeating the above procedures using N-acetylmorphine as amide.

The compound 1α,3β,22-trihydroxy-9,10-secochola-5(Z),7,10(19)-trien-24-oic acid N-methylanilide [Formula (I)—A=(A-2), $R^1=C_6H_5$, $R^2=CH_3$, $R^3=\alpha\text{-}CH_3$, $R^4=R^5=R^a=H$, $R^b=OH$, Y=valence bond] may similarly be prepared by repeating the above procedures using N-methylacetanilide as amide.

The compound 1α,3β,22-trihydroxy-9,10-secochola-5(Z),7,10(19)-trien-24-oic acid diethylamide [Formula (I)—A=(A-2), $R^1=R^2=C_2H_5$, $R^3=\alpha\text{-}CH_3$, $R^4=R^5=R^a=H$, $R^b=OH$, Y=valence bond] may similarly be prepared by repeating the above procedures using N,N-diethylacetamide as amide.

The compound 1α,3β,22-trihydroxy-9,10-secochola-5(E),7-dien-24-oic acid piperidine amide [Formula (I)—A=(A-5), $R^1+R^2=(CH_2)_5$, $R^3=\alpha\text{-}CH_3$, $R^4=R^5=R^a=H$, $R^b=OH$, Y=valence bond] may be prepared from N-acetylpiperidine and the product from Preparation 7(a) using the above procedures.

The compound 1α,3β,22-trihydroxy-9,10-secochola-5(Z),7-dien-24-oic acid piperidine amide [Formula (I)—A=(A-4), $R^1+R^2=(CH_2)_5$, $R^3=\alpha\text{-}CH_3$, $R^4=R^5=R^a=H$, $R^b=OH$, Y=valence bond] may be prepared from N-acetylpiperidine and the product from Preparation 7(b) using the above procedures.

The compound 1α,3β,22-trihydroxy-10-spirocyclopropyl-9,10-secochola-5(E),7-dien-24-oic acid piperidine amide [Formula (I)—A=(A-7), $R^1+R^2=(CH_2)_5$, $R^3=\alpha\text{-}CH_3$, $R^4=R^5=R^a=H$, $R^b=OH$, Y=valence bond] may be prepared from N-acetylpiperidine and the product from Preparation 7(c) using the above procedures.

The compound 1α,3β,22-trihydroxy-10-spirocyclopropyl-9,10-secochola-5(Z),7-dien-24-oic acid piperidine amide [Formula (I)—A=(A-6), $R^1+R^2=(CH_2)_5$, $R^3=\alpha\text{-}CH_3$, $R^4=R^5=R^a=H$, $R^b=OH$, Y=valence bond] may be prepared from N-acetylpiperidine and the product from Preparation 7(d) using the above procedures.

The compound 1α,3β,22-trihydroxy-19-nor-9,10-secochola-5,7-dien-24-oic acid piperidine amide [Formula (I)—A=(A-8), $R^1+R^2=(CH_2)_5$, $R^3=\alpha\text{-}CH_3$, $R^4=R^5=R^a=H$, $R^b=OH$, Y=valence bond] may be prepared from N-acetylpiperidine and 1α,3β-bis-t-butyldimethylsilyloxy-20α-formyl-19-nor-9,10-secopregna-5,7-diene [Formula (II)—A=(A-8), $R^3=\alpha\text{-}CH_3$, $R^4=R^5=t\text{-}Bu(Me)_2Si$, Y=valence bond] using the above procedures.

EXAMPLE 4 a) 1α,3β-Bis-triisopropylsilyloxy-20-epi-22-hydroxy-9,10-secochola-5(E),7,10(19)-trien-24-oic acid piperidine amide [Formula (I)—A=(A-3), $R^1+R^2=(CH_2)_5$, $R^3=\beta\text{-}CH_3$, $R^4=R^5=(i\text{-}Pr)_3Si$, $R^a=H$, $R^b=OH$, Y=valene bond]

A solution of N-acetylpiperidine (914 mg) in tetrahydrofuran (15 ml) was treated with lithium diisopropylamide (3 ml of a 2M solution in tetrahydrofuran, added dropwise), stirred for 1 hour at room temperature and then cooled to −78E. A portion of the solution (3.6 ml) was added dropwise to a solution of 1α,3β-bis-triisopropylsilyloxy-20R-formyl-9,10-secopregna-5(E),7,10(19)-triene [Formula (II)—A=(A-3), $R^3=\beta\text{-}CH_3$, $R^4=R^5=(i\text{-}Pr)_3Si$, Y=valence bond] (170 mg) in tetrahydrofuran (3 ml). The resulting mixture was allowed to warm to room temperature, quenched with saturated aqueous ammonium chloride, and the product was extracted into ethyl acetate and purified by chromatography on silica gel (eluting with ethyl acetate in hexane) to give the title compound (175 mg) as a mixture of 22R and 22S isomers. UV (Et$_2$O) $\lambda_{max}$ 272, 207, $\lambda_{min}$ 232 nm, $E_{max}/E_{min}$ 3.1; IR (CCl$_4$) $\nu_{max}$ 3600–3300 (OH), 1630, 1465 cm$^{-1}$; NMR (CDCl$_3$) δ 0.64 (s, 18-H's), 3.1–3.8 (m, NCH$_2$'s), 3.8–4.8 (m, 1,3,22-H's), 4.8–5.1 (bs, 19-H's), 5.6–6.6 (ABq, 6,7-H's).

b) 1α,3β-Bis-triisopropylsilyloxy-20-epi-22-hydroxy-9,10-secochola-5(Z),7,10(19)-trien-24-oic acid piperidine amide [Formula (I)—A=(A-2), $R^1+R^2=(CH_2)_5$, $R^3=\beta\text{-}CH_3$, $R^4=R^5=(i\text{-}Pr)_3Si$, $R^a=H$, $R^b=OH$, Y=valence bond]

A solution of the product from (a) above (45 mg) in benzene (6 ml) containing phenazine (21 mg) was photoisomerised by irradiation for 20 minutes. The product was worked up and isolated by chromatography to give the title compound (32 mg). UV (Et$_2$O) $\lambda_{max}$ 264, 207, $\lambda_{min}$ 227 nm, $E_{max}/E_{min}$ 1.8; IR (CDCl$_3$) $\nu_{max}$ 3660–3300 (OH), 1620, 1465 cm$^{-1}$; NMR (CDCl$_3$) δ 0.5 (s, 18-H's), 3.0–3.7 (m, NCH$_2$'s), 3.8–4.7 (m, 1,3,22-H's), 4.7, 5.3 (ea. s, 19-H's), 5.6–6.4 (ABq, 6,7-H's).

c) 20-Epi-1α,3β,22-trihydroxy-9,10-secochola-5(Z),7,10(19)-trien-24-oic acid piperidine amide [Formula (I)—A=(A-2), $R^1+R^2=(CH_2)_5$, $R^3=\beta\text{-}CH_3$, $R^4=R^5=R^a=H$, $R^b=OH$, Y=valence bond]

The product from (b) above (32 mg) in tetrahydrofuran (0.25 ml) was treated with tetrabutylammonium fluoride (0.25 ml of a 1M solution in tetrahydrofuran) at room temperature. After 3 hours the reaction mixture was worked up and the desilylated title compound (15 mg) was isolated by preparative thin layer chromatography. UV (EtOH) $\lambda_{max}$ 265, 207, $\lambda_{min}$ 228 nm, $E_{max}/E_{min}$ 1.8; IR (CDCl$_3$) $\nu_{max}$ 3660–3200 (OH), 1620, 1450 cm$^{-1}$; NMR (CDCl$_3$) δ 0.53 (s, 18-H's), 3.1–3.8 (m, NCH$_2$'s), 3.8–4.6 (m, 1,3,23-H's), 4.8, 5.4 (ea. s, 19-H's), 5.7–6.6 (ABq, 6,7-H's).

d) 22-Benzoyloxy-1α,3β-bis-triisopropylsilyloxy-20-epi-9,10-secochola-5(E),7,10(19)-trien-24-oic acid piperidine amide [Formula (I)—A=(A-3), $R^1+R^2=(CH_2)_5$, $R^3=\beta\text{-}CH_3$, $R^4=R^5=(i\text{-}Pr)_3Si$, $R^a=H$, $R^b=C_6H_5$, CO, Y=valence bond]

The mixture of 22R and 22S isomers from (a) above (40 mg) in pyridine (1.0 ml) was treated with benzoyl chloride (40 mg) for 3 hours at room temperature. Following work up it was found that the 22R and 22S benzoate esters could be resolved by thin layer chromatography (silica gel, eluting with ethyl acetate in hexane) to yield (i) the less polar isomer of the title compound (30 mg), UV (E$_2$O) $\lambda_{max}$ 271, $\lambda_{min}$ 226 nm, $E_{max}/E_{min}$ 2.8; IR (CDCl$_3$) $\nu_{max}$ 1710 (ester C=O), 1630, 1460 cm$^{-1}$; NMR (CDCl$_3$) δ 0.6 (s, 18-H's), 3.2–3.7 (m, NCH$_2$'s), 3.9–4.8 (m, 1,3-H's), 4.8–5.0 (bs, 19-H's), 5.5–6.5 (ABq, 6,7-H's), 6.9–8.1 (m, C$_6$H$_5$) and (ii) the more polar isomer of the title compound (14 mg).

e) 22-Benzoyloxy-1α,3β-bis-triisopropylsilyloxy-20-epi-9,10-secochola-5(Z), 7,10(19)-trien-24-oic acid piperidine amide (Isomer A) [Formula (I)—A=(A-2), $R^1+R^2=(CH_2)_5$, $R^3=\beta\text{-}CH_3$, $R^4=R^5=(i\text{-}Pr)_3Si$, $R^a=H$, $R^b=C_6H_5CO_2$, Y=valence bond]

A solution of the less polar isomer from (d) above, presumed on the basis of Cram's Rule to be 22R (50 mg) in benzene (5 ml) containing phenazine (20 mg) was photoisomerised by irradiation for 20 minutes. The product was worked up and isolated by chromatography to give the title compound (40 mg). UV (Et$_2$O) $\lambda_{max}$ 263, $\lambda_{min}$ 244nm, $E_{max}/E_{min}$ 1.1; IR (CDCl$_3$) $\nu_{max}$ 1705, 1625 cm$^{-1}$; NMR (CDCl$_3$) δ 0.6 (s, 18-H's), 3.3–3.8 (m, NCH's),4.0–4.8 (m, 1,3-H's), 4.8–5.3 (ea. s, 19-H's), 5.3–5.8 (m, 22-H's), 5.5–6.3 (ABq, 6,7-H's), 7.3–8.3 (m, Ar H's).

f) 22-Benzoyloxy-1α,3β-dihydroxy-20-epi-9,10-secochola-5(Z),7,10(19)-trien-24-oic acid piperidine amide (Isomer A) [Formula (I)—A=(A-2), $R^1+R^2=(CH_2)_5$, $R^3=\alpha\text{-}CH_3$, $R^4=R^5=R^a=H$, $R^b=C_6H_5CO_2$, Y=valence bond]

The product from (e) above (40 mg) in tetrahydrofuran (0.3 ml) was treated with tetrabutylammonium fluoride (0.3 ml of a 1M solution in tetrahydrofuran) at room temperature. After 3 hours the reaction mixture was worked up and the desilylated title compound (20 mg) was isolated by thin layer chromatography. UV (Et$_2$O) $\lambda_{max}$ 228, 265, $\lambda_{min}$ 247 nm, E$_{max}$/E$_{min}$ 1.1; IR (CDCl$_3$) $\nu_{max}$ 3700–3200 (OH), 1710, 1625 cm$^{-1}$; NMR (CDCl$_3$) δ 0.6 (s, 18-H's), 1.1 (d, 21-H's), 3.1–3.7 (m, NCH's), 3.8–4.6 (m, 1,3-H's), 4.7–5.6 (2 ea. s,m, 19,22-H's), 5.6–6.5 (ABq, 6,7-H's), 7.1–8.1 (m, Ar H's).

g) 22-Hydroxy-1α,3β-bis-triisopropylsilyloxy-20-epi-9,10-secochola-5(E),7,10(19)-trien-24-oic acid piperidine amide (Isomer A) [Formula (I)—A=(A-3), R$^1$+R$^2$=(CH$_2$)$_5$, R$^3$=β-CH$_3$, R$^4$=R$^5$=(i-Pr)$_3$Si, R$^a$=H, R$^b$=OH, Y=valence bond]

A solution of the less polar isomer from (d) above (140 mg) was treated with aqueous sodium hydroxide (0.2 ml, 2 M) in n-butanol (2 ml) for 2 days at room temperature. The products were worked up and isolated by thin layer chromatography. In addition to unreacted starting material (23 mg) and 22,23-alkene (35 mg) produced by elimination there was obtained the title compound (41 mg). IR (CDCl$_3$) $\nu_{max}$ 3600–3200, 1620, 1450 cm$^{-1}$; NMR (CDCl$_3$) δ 0.53 (s, 18-H's), 3.1–3.9 (m, NCH's),3.9–4.8 (m, 1,3-H's), 4.8–5.1 (bs, 19-H's), 5.6–6.7 (ABq, 6,7-H's).

h) 22-Hydroxy-1α,3β-bis-triisopropylsilyloxy-20-epi-9,10-secochola-5(Z),7,10(19)-trien-24-oic acid piperidine amide (Isomer A) [Formula (I)—A=(A-2), R$^1$+R$^2$=(CH$_2$)$_5$, R$^3$=β-CH$_3$, R$^4$=R$^5$=(i-Pr)$_3$Si, R$^a$=H, R$^b$=OH, Y=valence bond]

A solution of the product from (g) above (41 mg) in benzene (5 ml) containing phenazine (20 mg) was photoisomerised by irradiation for 20 minutes. The product was worked up and isolated by chromatography to give the title compound (30 mg). UV (Et$_2$O) $\lambda_{max}$ 262, $\lambda_{min}$ 227nm, E$_{max}$/E$_{min}$ 1.5; IR (CDCl$_3$) $\nu_{max}$ 3650–3200 (OH), 1615, 1450 cm$^{-1}$; NMR (CDCl$_3$) δ 0.53 (s, 18-H's), 3.1–3.8 (m, NCH$_2$'s),4.0–4.6 (m, 1,3,22-H's), 4.7, 5.3 (ea. s, 19-H's), 5.7–6.3 (ABq, 6,7-H's).

i) 1α,3β,22-Trihydroxy-20-epi-9,10-secochola-5(Z),7,10(19)-trien-24-oic acid piperidine amide (Isomer A) [Formula (I)—A=(A-2), R$^1$+R$^2$=(CH$_2$)$_5$, R$^3$=β-CH$_3$, R$^4$=R$^5$=R$^a$=H, R$^b$=OH, Y=valence bond]

The product from (h) above (30 mg) in tetrahydrofuran (0.25 ml) was treated with tetrabutylammonium fluoride (0.25 ml of a 1M solution in tetrahydrofuran) at room temperature. After 3 hours the reaction mixture was worked up and the desilylated title compound (17 mg) was isolated by preparative thin layer chromatography. UV (EtOH) $\lambda_{max}$ 263, $\lambda_{min}$ 227 nm, E$_{max}$/E$_{min}$ 1.6; IR (CDCl$_3$) $\nu_{max}$ 3640–3140 (OH), 1610, 1445 cm$^{-1}$; NMR (CDCl$_3$) δ 0.53 (s, 18-H's), 0.88 (d, 21-H's), 3.1–3.8 (m, NCH$_2$'s), 4.0–4.6 (m, 1,3,22-H's), 4.8, 5.4 (ea. s, 19-H's), 5.7–6.8 (ABq, 6,7-H's) .

The compound 1α,3β,22-trihydroxy-20-epi-9,10-secochola-5(Z),7,10(19)-trien-24-oic acid dimethylamide [Formula (I)—A=(A-2), R$^1$=R$^2$=CH$_3$, R$^3$=β-CH$_3$, R$^4$=R$^5$=R$^a$=H, R$^b$=OH, Y=valence bond] may be prepared by repeating the above procedures using N,N-dimethylacetamide in place of the N-acetylpiperidine in step (a).

The compound 1α,3β,22-trihydroxy-20-epi-9,10-secochola-5(Z),7,10(19)-trien-24-oic acid morpholine amide [Formula (I)—A=(A-2), R$^1$+R$^2$=(CH$_2$)$_2$O (CH$_2$)$_2$, R$^3$=β-CH$_3$, R$^4$=R$^5$=R$^a$=H, R$^b$=OH, Y=valence bond] may be prepared by repeating the above procedures using N-acetylmorphine in place of the N-acetylpiperidine in step (a).

The compound 1α,3β,22-trihydroxy-20-epi-9,10-secochola-5(Z),7,10(19)-trien-24-oic acid N,N-dicyclopropylamide [Formula (I)—A=(A-2), R$^1$=R$^2$=cyclopropyl, R$^3$=β-CH$_3$, R$^4$=R$^5$=R$^a$=H, R$^b$=OH, Y=valence bond] may be prepared by repeating the above procedures using N,N-dicyclopropylacetamide in place of the N-acetylpiperidine in step (a).

The compound 1α,3β,22-trihydroxy-20-epi-9,10-secochola-5(Z),7,10(19)-trien-24-oic acid diethylamide [Formula (I)—A=(A-2), R$^1$=R$^2$=C$_2$H$_5$, R$^3$=β-CH$_3$, R$^4$=R$^5$=R$^a$=H, R$^b$=OH, Y=valence bond] may be prepared by repeating the above procedures using N,N-diethylacetamide in place of the N-acetylpiperidine in step (a).

EXAMPLE 5 a) 1α,3β-Bis-triisopropylsilyloxy-22-hydroxy-20-epi-9,10-secochola-5(E),7,10(19)-trien-24-oic acid diisopropylamide [Formula (I)—A=(A-3), R$^1$=R$^2$=i-Pr, R$^3$=β-CH$_3$, R$^4$=R$^5$=(i-Pr)$_3$Si, R$^a$=H, R$^b$=OH, Y=valence bond]

A solution of N,N-diisopropylacetamide (1.03 g) in tetrahydrofuran (15 ml) was treated with lithium diisopropylamide (3 ml of a 2M solution in tetrahydrofuran, added dropwise), stirred for 1 hour at room temperature and then cooled to −78E. A solution of 1α,3β-bis-triisopropylsilyloxy-20R-formyl-9,10-secopregna-5(E),7,10 (19)-triene [Formula (II)—A=(A-3), R$^3$=β-CH$_3$, R$^4$=R$^5$=(i-Pr)$_3$Si, Y=valence bond] (120 mg) in tetrahydrofuran (2 ml) was treated at −78E with a portion of the thus-obtained enolate solution (2.9 ml, added dropwise). The temperature was maintained at −78E for 15 minutes, whereafter the reaction mixture was quenched with saturated aqueous ammonium chloride, and the product was extracted into ethyl acetate and purified by chromatography to give (A) the less polar isomer of the title compound (13 mg): UV (Et$_2$O) $\lambda_{max}$ 268, $\lambda_{min}$ 227 nm, E$_{max}$/E$_{min}$ 4.4 and (B) the more polar isomer (52 mg): UV (Et$_2$O) $\lambda_{max}$ 269 nm; IR (CDCl$_3$) $\nu_{max}$ 3600–3200 (OH), 1620, 1450 cm$^{-1}$; NMR (CDCl$_3$) δ 0.56 (s, 18-H's), 3.2–4.7(m, NCH's, 1,3,22-H's), 4.7–5.0 (bs, 19-H's), 5.4–6.6 (ABq, 6,7-H's).

b) 1α,3β-Bis-triisopropylsilyloxy-22-hydroxy-20-epi-9,10-secochola-5(Z),7,10(19)-trien-24-oic acid diisopropylamide (Isomer B) [Formula (I)—A=(A-2), R$^1$=R$^2$=i-Pr, R$^3$=β-CH$_3$, R$^4$=R$^5$=(i-Pr)$_3$Si, R$^a$=H, R$^b$=OH, Y=valence bond]

A solution of the more polar isomer from (a) above (52 mg) in benzene (6.5 ml) containing phenazine (23 mg) was photoisomerised by irradiation for 40 minutes. The product was worked up and isolated by chromatography to give the title compound (40 mg). UV (Et$_2$O) $\lambda_{max}$ 263, $\lambda_{min}$ 226 nm, E$_{max}$/E$_{min}$ 1.4; IR (CDCl$_3$) $\nu_{max}$ 3600–3200 (OH), 1615, 1450 cm$^{-1}$; NMR (CDCl$_3$) δ 0.5 (s, 18-H's), 3.3–4.6 (m, NCH's, 1,3,22-H's), 4.6–5.3 (ea. s, 19-H's), 5.6–6.4 (ABq, 6,7-H's).

c) 1α,3β,22-Trihydroxy-20-epi-9,10-secochola-5(Z),7,10 (19)-trien-24-oic acid diisopropylamide (Isomer B) [Formula (I)—A=(A-2), R$^1$=R$^2$=i-Pr, R$^3$=β-CH$_3$, R$^4$=R$^5$=R$^a$=H, R$^b$=OH, Y=valence bond]

The product from (b) above (40 mg) in tetrahydrofuran (0.3 ml) was treated with tetrabutylammonium fluoride (0.3 ml of a 1M solution in tetrahydrofuran) at room temperature. After 4 hours the reaction mixture was worked up and the desilylated title compound (16 mg) was isolated by thin layer chromatography. UV (EtOH) $\lambda_{max}$ 263, $\lambda_{min}$ 227 nm, E$_{max}$/E$_{min}$ 1.6; IR (CDCl$_3$) $\nu_{max}$ 3640–3160 (OH), 1620, 1450 cm$^{-1}$; NMR (CDCl$_3$) δ 0.53 (s, 18-H's), 0.87 (d, 21-H's), 3.0–4.6 (m, NCH's, 1,3,22-H's), 5.0–5.3 (ea. s, 19-H's), 5.6–6.5 (ABq, 6,7-H's).

EXAMPLE 6 a) 1α,3β-Bis-triisopropylsilyloxy-20-epi-23-homo-23-hydroxy-9,10-secochola-5(E),7,10(19)-trien-24-oic acid piperidine amide [Formula (I)—A=(A-3), $R^1+R^2=(CH_2)_5$, $R^3$=β-$CH_3$, $R^4=R^5$=(i-Pr)$_3$Si, $R^a$=H, $R^b$=OH, Y=$CH_2$]

A solution of N-acetylpyridine (457 mg) in tetrahydrofuran (13.5 ml) was treated with lithium diisopropylamide (1.5 ml of a 2M solution in tetrahydrofuran, added dropwise), stirred for 1 hour at room temperature and then cooled to −78E. A solution of 1α,3β-bis-triisopropylsilyloxy -20(epi) -formylmethyl-9,10-secopregna-5(E),7,10(19)-triene [Formula (II)—A=(A-3), $R^3$=β-$CH_3$, $R^4=R^5$=(i-Pr)$_3$Si, Y=$CH_2$] (75 mg) in tetrahydrofuran (2 ml) was treated at −78E with a portion of the thus-obtained enolate solution (2.5 ml, added dropwise). The reaction mixture was allowed to warm to room temperature and stood for 3 hours, whereafter it was quenched with saturated aqueous ammonium chloride, and the product was extracted into diethyl ether and purified by chromatography on silica gel (eluting with ethyl acetate in hexane) to give unreacted starting material (20 mg) and the title compound (175 mg) as a mixture of 23R and 23S isomers. UV (Et$_2$O) $\lambda_{max}$ 269 nm; IR (CDCl$_3$) $\nu_{max}$ 3600–3320 (OH), 1635, 1470 cm$^{-1}$; NMR (CDCl$_3$) δ 0.51 and 0.56 (s, 18-H's), 3.1–3.6 (m, NCH$_2$'s), 3.6–4.7 (m, 1,3,23-H's), 4.7–5.0 (bs, 19-H's), 5.6–6.6 (ABq, 6,7-H's).

b) 1α,3β-Bis-triisopropylsilyloxy-20-epi-23-homo-23-hydroxy-9,10-secochola-5(Z),7,10(19)-trien-24-oic acid piperidine amide [Formula (I)—A=(A-2), $R^1+R^2=(CH_2)_5$, $R^3$=β-$CH_3$ $R^4=R^5$=(i-Pr)$_3$Si, $R^a$=H, $R^b$=OH, Y=$CH_2$]

A solution of the mixed 23R and 23S isomers from (a) above (60 mg) in benzene (7.5 ml) containing phenazine (27 mg) was photoisomerised by irradiation for 35 minutes. The products were worked up and isolated by chromatography to give (A) the less polar isomer of the title compound (30 mg): UV (Et$_2$O) $\lambda_{max}$ 264, $\lambda_{min}$ 227 nm, $E_{max}/E_{min}$ 1.9; IR (CDCl$_3$) $\nu_{max}$ 3600–3320 (OH), 1635, 1470 cm$^{-1}$; NMR (CCl$_4$) δ 0.53 (s, 18-H's), 3.0–3.6 (m, NCH$_2$'s), 3.6–4.6 (m, 1,3,23-H's), 4.6, 5.2 (ea. s, 19-H's), 5.5–6.3 (ABq, 6,7-H's) and (B) the more polar isomer (24 mg): UV (Et$_2$O) $\lambda_{max}$ 265, $\lambda_{min}$ 227 nm, $E_{max}/E_{min}$ 1.9; IR (CCl$_4$) $\nu_{max}$ 3600–3300 (OH), 1635, 1470 cm$^{-1}$; NMR (CCl$_4$) δ 0.5(s, 18-H's), 3.0–3.6 (m, NCH$_2$'s), 3.6–4.6 (m, 1,3,23-H's), 4.6, 5.3 (ea. s, 19-H's), 5.6–6.5 (ABq, 6,7-H's).

c) 1α,3β,23-Trihydroxy-20-epi-23-homo-9,10-secochola-5(Z),7,10(19)-trien-24-oic acid piperidine amide (Isomer B) [Formula (I)—A=(A-2), $R^1+R^2=(CH_2)_5$, $R^3$=β-$CH_3$, $R^4=R^5=R^a$=H, $R^b$=OH, Y=$CH_2$]

The more polar isomer from (b) above (24 mg) in tetrahydrofuran (0.18 ml) was treated with tetrabutylammonium fluoride (0.18 ml of a 1M solution in tetrahydrofuran) at room temperature. After 3 hours the reaction mixture was worked up and the desilylated title compound (13 mg) was isolated by preparative thin layer chromatography. UV (EtOH) $\lambda_{max}$ 265, $\lambda_{min}$ 220 nm, $E_{max}/E_{min}$ 2.0; IR (CDCl$_3$) $\nu_{max}$ 3640–3300 (OH), 1620, 1450 cm$^{-1}$; NMR (CDCl$_3$) δ 0.5 (s, 18-H's), 0.83 (d, 21-H's), 3.1–3.7 (m, NCH$_2$'s), 3.7–4.6 (m, 1,3,23-H's), 4.7, 5.4 (ea. s, 19-H's), 5.6–6.6 (ABq, 6,7-H's).

d) 1α,3β,23-Trihydroxy-20-epi-23-homo-9,10-secochola-5(Z),7,10(19)-trien-24-oic acid piperidine amide (Isomer A) [Formula (I)—A=(A-2), $R^1+R^2=(CH_2)_5$, $R^3$=β-$CH_3$, $R^4=R^5=R^a$=H, $R^b$=OH, Y=$CH_2$]

The less polar isomer from (b) above (30 mg) in tetrahydrofuran (0.24 ml) was treated with tetrabutylammonium fluoride (0.24 ml of a 1M solution in tetrahydrofuran) at room temperature. After 3 hours the reaction mixture was worked up and the desilylated title compound (13 mg) was isolated by preparative thin layer chromatography. UV (EtOH) $\lambda_{max}$ 266, $\lambda_{min}$ 228 nm, $E_{max}/E_{min}$ 2.0; IR (CDCl$_3$) $\nu_{max}$ 3640–3240 (OH) , 1620, 1450 cm$^{-1}$; NMR (CDCl$_3$) δ 0.56 (s, 18-H's), 3.0–3.7 (m, NCH$_2$'s), 3.7–4.5 (m, 1,3,23-H's), 4.7, 5.5 (ea. s, 19-H's), 5.6–6.6 (ABq, 6,7-H's).

The compound 1α,3β,23-trihydroxy-20-epi-23-homo-9,10-secochola-5(Z),7,10(19)-trien-24-oic acid dimethylamide [Formula (I)—A=(A-2), $R^1=R^2=CH_3$, $R^3$=β-$CH_3$, $R^4=R^5=R^a$=H, $R^b$=OH, Y=$CH_2$] may be prepared by repeating the above procedures using N,N-dimethylacetamide in place of the N-acetylpiperidine in step (a).

The compound 1α,3β,23-trihydroxy-20-epi-23-homo-9,10-secochola-5(Z),7,10(19)-trien-24-oic acid morpholine amide [Formula (I)—A=(A-2), $R^1+R^2=(CH_2)_2O(CH_2)_2$, $R^3$=β-$CH_3$, $R^4=R^5=R^a$=H, $R^b$=OH, Y=$CH_2$] may be prepared by repeating the above procedures using N-acetylmorphine in place of the N-acetylpiperidine in step (a).

The compound 1α,3β,23-trihydroxy-20-epi-23-homo-9,10-secochola-5(Z),7,10(19)-trien-24-oic acid N-methylanilide [Formula (I)—A=(A-2), $R^1=C_6H_5$, $R^2=CH_3$, $R^3$=β-$CH_3$, $R^4=R^5=R^a$=H, $R^b$=OH, Y=$CH_2$] may be prepared by repeating the above procedures using N-methylacetanilide in place of the N-acetylpiperidine in step (a).

The compound 1α,3β,23-trihydroxy-20-epi-23-homo-9,10-secochola-5(Z),7,10(19)-trien-24-oic acid diethylamide [Formula (I)—A=(A-2), $R^1=R^2=C_2H_5$, $R^3$=β-$CH_3$, $R^4=R^5=R^a$=H, $R^b$=OH, Y=$CH_2$] may be prepared by repeating the above procedures using N,N-diethylacetamide in place of the N-acetylpiperidine in step (a).

The compound 1α,3β,23-trihydroxy-20-epi-23-homo-9,10-secochola-5(Z),7,10(19)-trien-24-oic acid N,N-dicyclopropylamide [Formula (I)—A=(A-2), $R^1=R^2$=cyclopropyl, $R^3$=β-$CH_3$, $R^4=R^5=R^a$=H, $R^b$=OH, Y=$CH_2$] may be prepared by repeating the above procedures using N,N-dicyclopropylacetamide in place of the N-acetylpiperidine in step (a). procedures.

The compound 1α,3β,23-trihydroxy-23-homo-9,10-secochola-5(E),7-dien-24-oic acid piperidine amide [Formula (I)—A=(A-5), $R^1+R^2=(CH_2)_5$, $R^3$=α-$CH_3$, $R^4=R^5=R^a$=H, $R^b$=OH, Y=$CH_2$] may be prepared from N-acetylpiperidine and the product from Preparation 8(a) using the above The compound 1α,3β,23-trihydroxy-23-homo-9,10-secochola-5(E),7-dien-24-oic acid piperidine amide [Formula (I)—A=(A-5), $R^1+R^2=(CH_2)_5$, $R^3$=α-$CH_3$, $R^4=R^5=R^a$=H, $R^b$=OH, Y=$CH_2$] may be prepared from N-acetylpiperidine and the product from Preparation 8(b) using the above The compound 1α,3β,23-trihydroxy-23-homo-10-spirocyclopropyl-9,10-secochola-5(E),7-dien-24-oic acid piperidine amide [Formula (I)—A=(A-7), $R^1+R^2=(CH_2)_5$, $R^3$=α-$CH_3$, $R^4=R^5=R^a$=H, $R^b$=OH, Y=$CH_2$] may be prepared from N-acetylpiperidine and the product from Preparation 8(c) using the above procedures.

The compound 1α,3β,23-trihydroxy-23-homo-10-spirocyclopropyl-9,10-secochola-5(Z),7-dien-24-oic acid piperidine amide [Formula (I)—A=(A-6), $R^1+R^2=(CH_2)_5$, $R^3$=α-$CH_3$, $R^4=R^5=R^a$=H, $R^b$=OH, Y=$CH_2$] may be prepared from N-acetylpiperidine and the product from Preparation 8(d) using the above procedures.

The compound 1α,3β,23-trihydroxy-23-homo-19-nor-9,10-secochola-5,7-dien-24-oic acid piperidine amide [Formula (I)—A=(A-8), $R^1+R^2=(CH_2)_5$, $R^3$=α-$CH_3$, $R^4=R^5=R^a$=H, $R^b$=OH, Y=$CH_2$] may be prepared from N-acetylpiperidine and the product from Preparation 8(e) using the above procedures.

EXAMPLE 7 a) 1α,3β-Bis-triisopropylsilyloxy-20-epi-22-hydroxy-9,10-secochola-5(E),7,10(19)-trien-24-oic acid piperidine amide [Formula (I)—A=(A-3), $R^1+R^2$=(CH$_2$)$_5$, $R^3$=β-CH$_3$, $R^4$=$R^5$=(i-Pr)$_3$Si, $R^a$=H, $R^b$=OH, Y=valene bond]

Potassium hydride (0.1 ml of a 35% dispersion in mineral oil) was added dropwise to a solution of 1α,3β-bis-triisopropylsilyloxy-20-epi-22-hydroxy-9,10-secochola-5(E),7,10(19)-trien-24-oic-acid piperidine amide [Formula (I)—A=(A-3), $R^1+R^2$=(CH$_2$)$_5$, $R^3$=β-CH$_3$, $R^4$=$R^5$=(i-Pr)$_3$Si, $R^a$=H, $R^b$=OH, Y=valence bond] (125 mg), 18-crown-6 (50 mg) and methyl iodide (100 μl) in tetrahydrofuran (3 ml) at −10°. The mixture was stirred at −10° for 45 minutes, then quenched with ice. The product was extracted into ether, worked up and isolated by column chromatography to give the title compound (100 mg). UV (Et$_2$O) λ$_{max}$ 268, λ$_{min}$ 230 nm, E$_{max}$/E$_{min}$ 3.7; IR (CDCl$_3$) ν$_{max}$ 1615, 1440 cm$^{-1}$; NMR (CDCl$_3$) δ 0.56 (s, 18-H's), 3.0–3.7 (m, NCH$_2$'s), 3.3 (s, OMe), 3.7–4.8 (m, 1,3, 22-H's), 4.8–5.1 (bs, 19-H's), 5.5–6.8 (ABq, 6,7-H's).

b) 1α,3β-Bis-triisopropylsilyloxy-20-epi-22-methoxy-9,10-secochola-5(Z),7,10(19)-trien-24-oic acid piperidine amide [Formula (I)—A=(A-2), $R^1+R^2$=(CH$_2$)$_5$, $R^3$=β-CH$_3$, $R^4$=$R^5$=(i-Pr)$_3$Si, $R^a$=H, $R^b$=OCH$_3$, Y=valene bond]

The product from (a) above (100 mg) in benzene (10 ml) containing phenazine (45 mg) was photoisomerised by irradiation for 1 hour. The product was worked up and isolated by chromatography to give the title compound (80 mg). UV (Et$_2$O) λ$_{max}$ 262, λ$_{min}$ 226 nm, E$_{max}$/E$_{min}$ 1.5; IR (CDCl$_3$) ν$_{max}$ 1615, 1460 cm$^{-1}$; NMR (CDCl$_3$) δ 0.5 (s, 18-H's), 3.0–3.6 (m, NCH$_2$'s), 3.23 (s, OMe), 3.7–4.8 (m, 1,3,22-H's), 4.6, 5.3 (ea. s, 19-H's), 5.6–6.2 (ABq, 6,7-H's).

c) 1α,3β-Dihydroxy-20-epi-22-methoxy-9,10-secochola-5(Z),7,10(19)-trien-24-oic acid piperidine amide [Formula (I)—A=(A-2), $R^1+R^2$=(CH$_2$)$_5$, $R^3$=β-CH$_3$, $R^4$=$R^5$=H, $R^a$=H, $R^b$=OCH$_3$, Y=valence bond]

The product from (b) above (100 mg) in tetrahydrofuran (0.6 ml) was treated with tetrabutylammonium fluoride (0.6 ml of a 1M solution in tetrahydrofuran) at room temperature. After 4 hours the reaction mixture was worked up and the desilylated title compound (38 mg) was isolated by thin layer chromatography. UV (Et$_2$O) λ$_{max}$ 263, λ$_{min}$ 227 nm, E$_{max}$/E$_{min}$ 1.6; IR (CDCl$_3$) ν$_{max}$ 3600–3200, 1610, 1440 cm$^{-1}$; NMR (CDCl$_3$) δ 0.5 (s, 18-H's), 3.1–3.6 (m, NCH$_2$'s), 3.23 (s, OMe), 3.6–4.6 (m, 1,3,22-H's), 4.7, 5.4 (ea. s, 19-H's), 5.6–6.6 (ABq, 6,7-H's).

The compound 1α,3β-dihydroxy-20-epi-22-ethoxy-9,10-secochola-5(Z),7,10(19)-trien-24-oic acid piperidine amide [Formula (I)—A=(A-2), $R^1+R^2$=(CH$_2$)$_5$, $R^3$=β-CH$_3$, $R^4$=$R^5$=$R^a$=H, $R^b$=OC$_2$H$_5$, Y=valence bond] may be prepared by using ethyl iodide in place of methyl iodide in step (a) above.

The compound 1α,3β-dihydroxy-20-epi-22-propoxy-9,10-secochola-5(Z),7,10(19)-trien-24-oic acid piperidine amide [Formula (I)—A=(A-2), $R^1+R^2$=(CH$_2$)$_5$, $R^3$=β-CH$_3$, $R^4$=$R^5$=$R^a$=H, $R^b$=OC$_3$H$_7$, Y=valence bond] may be prepared by using propyl iodide in place of methyl iodide in step (a) above.

The compound 1α,3β-dihydroxy-20-epi-23-methoxy-9,10-secochola-5(Z),7,10(19)-trien-24-oic acid piperidine amide [Formula (I)—A=(A-2), $R^1+R^2$=(CH$_2$)$_5$, $R^3$=β-CH$_3$, $R^4$=$R^5$=$R^b$=H, $R^a$=OCH$_3$, Y=valence bond] may be obtained by reacting 1α,3β-bis-triisopropylsilyloxy-20-epi-23-hydroxy-9,10-secochola-5(E),7,10(19)-trien-24-oic acid piperidine amide [Formula (I)—A=(A-3), $R^1+R^2$=(CH$_2$)$_5$, $R^3$=β-CH$_3$, $R^4$=$R^5$=(i-Pr)$_3$Si, $R^a$=OH, $R^b$=H, Y=valence bond] in accordance with the above procedures.

The compound 1α,3β-dihydroxy-23-methoxy-9,10-secochola-5(Z),7,10(19)-trien-24-oic acid piperidine amide [Formula (I)—A=(A-2), $R^1+R^2$=(CH$_2$)$_5$, $R^3$=α-CH$_3$, $R^4$=$R^5$=$R^b$=H, $R^a$=OCH$_3$, Y=valence bond] may be obtained by reacting 1α,3β-bis-triisopropylsilyloxy-23-hydroxy-9,10-secochola-5(E),7,10(19)-trien-24-oic acid piperidine amide [Formula (I)—A=(A-3), $R^1+R^2$=(CH$_2$)$_5$, $R^3$=α-CH$_3$, $R^4$=$R^5$=(i-Pr)$_3$Si, $R^a$=OH, $R^b$=H, Y=valence bond] in accordance with the above procedures.

The compound 1α,3β-dihydroxy-20-epi-23-methoxy-9,10-secochola-5(Z),7,10(19)-trien-24-oic acid diisopropylamide [Formula (I)—A=(A-2), $R^1$=$R^2$=i-Pr, $R^3$=β-CH$_3$, $R^4$=$R^5$=$R^b$=H, $R^a$=OCH$_3$, Y=valence bond] may be obtained by reacting 1α,3β-bis-triisopropylsilyloxy-20-epi-23-hydroxy-9,10-secochola-5(E),7,10(19)-trien-24-oic acid diisopropylamide [Formula (I)—A=(A-3), $R^1$=$R^2$=i-Pr, $R^3$=β-CH$_3$, $R^4$=$R^5$=(i-Pr)$_3$Si, $R^a$=OH, $R^b$=H, Y=valence bond] in accordance with the above procedures.

The compound 1α,3β-dihydroxy-20-epi-23-methoxy-9,10-secochola-5(Z),7,10(19)-trien-24-oic acid diethylamide [Formula (I)—A=(A-2), $R^1$=$R^2$=C$_2$H$_5$, $R^3$=β-CH$_3$, $R^4$=$R^5$=$R^b$=H, $R^a$=OCH$_3$, Y=valence bond] may be obtained by reacting 1α,3β-bis-triisopropylsilyloxy-20-epi-23-hydroxy-9,10-secochola-5(E),7,10(19)-trien-24-oic acid diethylamide [Formula (I)—A=(A-3), $R^1$=$R^2$=C$_2$H$_5$, $R^3$=β-CH$_3$, $R^4$=$R^5$=(i-Pr)$_3$Si, $R^a$=OH, $R^b$=H, Y=valence bond] in accordance with the above procedures.

The compound 1α,3β-dihydroxy-20-epi-22-methoxy-9,10-secochola-5(Z),7,10(19)-trien-24-oic acid diisopropylamide [Formula (I)—A=(A-2), $R^1$=$R^2$=i-Pr, $R^3$=β-CH$_3$, $R^4$=$R^5$=$R^a$=H, $R^b$=OCH$_3$, Y=valence bond] may be obtained by reacting 1α,3β-bis-triisopropylsilyloxy-20-epi-22-hydroxy-9,10-secochola-5(E),7,10(19)-trien-24-oic acid diisopropylamide [Formula (I)—A=(A-3), $R^1$=$R^2$=i-Pr, $R^3$=β-CH$_3$, $R^4$=$R^5$=(i-Pr)$_3$Si, $R^a$=H, $R^b$=OH, Y=valence bond] in accordance with the above procedures.

The compound 1α,3β-dihydroxy-22-methoxy-9,10-secochola-5(Z),7,10(19)-trien-24-oic acid diisopropylamide [Formula (I)—A=(A-2), $R^1$=$R^2$=i-Pr, $R^3$=α-CH$_3$, $R^4$=$R^5$=$R^a$=H, $R^b$=OCH$_3$, Y=valence bond] may be obtained by reacting 1α,3β-bis-triisopropylsilyloxy-22-hydroxy-9,10-secochola-5(E),7,10(19)-trien-24-oic acid diisopropylamide [Formula (I)—A=(A-3), $R^1$=$R^2$i-Pr, $R^3$=α-CH$_3$, $R^4$=$R^5$=(i-Pr)$_3$Si, $R^a$=H, $R^b$=OH, Y=valence bond] in accordance with the above procedures.

The compound 1α,3β-dihydroxy-20-epi-23-homo-23-methoxy-9,10-secochola-5(E),7,10(19)-trien-24-oic acid piperidine amide [Formula (I)—A=(A-3), $R^1+R^2$=(CH$_2$)$_5$, $R^3$=β-CH$_3$, $R^4$=$R^5$=$R^a$=H, $R^b$=OCH$_3$, Y=CH$_2$] may be obtained by reacting 1α,3β-bis-triisopropylsilyloxy-20-epi-23-homo-23-hydroxy-9,10-secochola-5(E),7,10(19)-trien-24-oic acid piperidine amide [Formula (I)—A=(A-3), $R^1+R^2$=(CH$_2$)$_5$, $R^3$=β-CH$_3$, $R^4$=$R^5$=(i-Pr)$_3$Si, $R^a$=H, $R^b$=OH, Y=CH$_2$] in accordance with the above procedures.

The compound 1α,3β-dihydroxy-22-methoxy-19-nor-9,10-secochola-5,7-dien-24-oic acid piperidine amide [Formula (I)—A=(A-8), $R^1+R^2$=(CH$_2$)$_5$, $R^3$=α-CH$_3$, $R^4$=$R^5$=$R^a$=H, $R^b$=OCH$_3$, Y=valence bond] may be obtained by reacting 1α,3β-bis-t-butyldimethylsilyloxy-22-hydroxy-19-nor-9,10-secochola-5,7-dien-24-oic acid piperidine amide [Formula (I)—A=(A-3), $R^1+R^2$=(CH$_2$)$_5$, $R^3$=α-CH$_3$, $R^4$=$R^5$=t-Bu(Me)$_2$Si, $R^a$=H, $R^b$=OH, Y=valence bond] in accordance with the above procedures.

We claim:
1. Compounds of general formula (I)

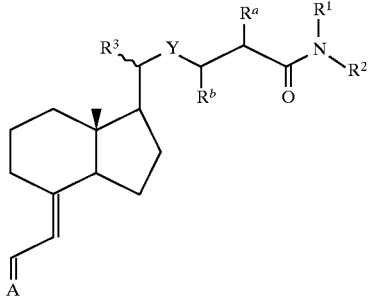

where $R^1$ and $R^2$, which may be the same or different, each represent a hydrogen atom or an aliphatic, cycloaliphatic, araliphatic or aryl group or together with the nitrogen atom to which they are attached form a heterocyclic group; $R^3$ represents a methyl group having α- or β-configuration; one of $R^a$ and $R^b$ represents a hydroxy group or protected hydroxy group and the other represents a hydrogen atom; Y represents a valence bond or an alkylene group containing up to 3 carbon atoms; and A= represents a cyclohexylidene moiety characteristic of the A-ring of a 1α-hydroxylated vitamin D or analogue thereof.

2. Compounds as claimed in claim 1 in which $R^1$ and $R^2$ are each selected from hydrogen atoms, lower alkyl, lower cycloalkyl, $C_{6-12}$ aryl $C_{1-4}$ alkyl and optionally substituted $C_{6-12}$ aryl groups.

3. Compounds as claimed in claim 2 in which $R^1$ and $R^2$ are each selected from methyl, ethyl, isopropyl and phenyl groups.

4. Compounds as claimed in claim 1 in which $R^1R^2N-$ represents a heterocyclic group comprising one or more 5- and/or 6-membered rings and optionally containing one or more further heteroatoms selected from O, N and S.

5. Compounds as claimed in claim 4 in which $R^1R^2N-$ represents piperidino or morpholino.

6. Compounds as claimed in claim 1 in which one of $R^a$ and $R^b$ represents a protected hydroxy group wherein the protecting group is a lower alkyl group optionally interrupted by one or more oxygen atoms.

7. Compounds as claimed in claim 1 in which A= represents one of the groups

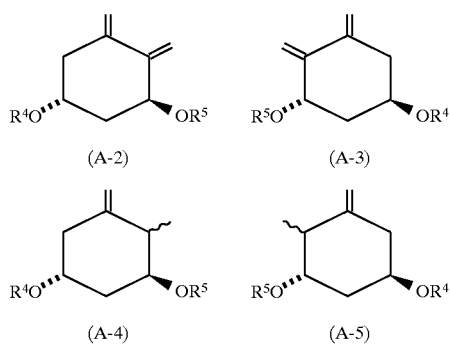

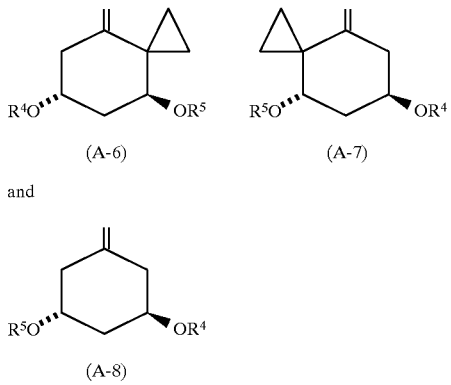

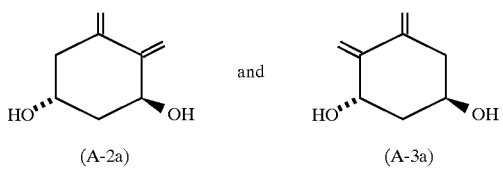

where $R^4$ and $R^5$ are each selected from hydrogen atoms and O-protecting groups.

8. Compounds as claimed in claim 7 in which $R^4$ and $R^5$ represent etherifying silyl groups.

9. Compounds as claimed in claim 7 in which $R^4$ and $R^5$ are selected from hydrogen atoms and metabolically labile etherifying or esterifying groups.

10. Compounds as claimed in claim 1 wherein A= represents one of the groups 11. 20,20-Dimethyl, 20-methylene and 20-spirocyclopropyl analogues of compounds as claimed in claim 1.

12. Pharmaceutical compositions comprising an active compound as claimed in claim 1 in admixture with one or more physiologically acceptable carriers or excipients.

13. A method of treatment of a human or animal subject to promote treatment of osteoporosis, wound healing, suppression of parathyroid hormone or neoplastic disease, infection, bone disease, autoimmune disease, host-graft reaction, transplant rejection, inflammatory disease, neoplasia, hyperplasia, myopathy, enteropathy, spondylitic heart disease, dermatological disease, rheumatoid arthritis, psoriatic arthritis, or secondary hyperparathyroidism, comprising administration to said subject of an effective amount of an active compound as claimed in claim 1.

* * * * *